United States Patent [19]
Sturley et al.

[11] Patent Number: 6,100,077
[45] Date of Patent: Aug. 8, 2000

[54] ISOLATION OF A GENE ENCODING DIACYLGLYCEROL ACYLTRANSFERASE

[75] Inventors: Stephen L. Sturley; Peter Oelkers, both of New York, N.Y.

[73] Assignee: The Trustees of Columbia University in the City of New York, New York, N.Y.

[21] Appl. No.: 09/165,042

[22] Filed: Oct. 1, 1998

[51] Int. Cl.[7] .............................. C12N 9/10; C12N 15/54
[52] U.S. Cl. ...................... 435/193; 435/183; 435/69.1; 435/320.1; 435/252.3; 435/325; 536/23.1; 536/23.2; 536/254.2; 536/410; 536/348
[58] Field of Search ...................... 435/193, 183, 435/69.1, 320.1, 252.3, 325, 254.2, 410, 348; 536/23.1, 23.2

[56] References Cited

PUBLICATIONS

Cases et al. Identification of a gene encoding an acyl CoA:diacylglycerol acyltransferase, a key enzyme in triacylglycerol synthesis, Proc. Natl. Acad. Sci. USA, 95: 13018–13023, Oct. 1998.
Sturley, S.L. et al. (1997) *Curr. Opin. Lipidol.* 8, 167–173 (Exhibit 1).
Yang, H. et al. (1996) *Science* 272, 1353–1356. (Exhibit 2).
Yu, C. et al. (1996) *J. Biol. Chem.* 271, 24157–24163. (Exhibit 3).
Chang, C.C.Y et al. (1993) *J. Biol. Chem.* 268, 20747–20755 (Exhibit 4).
Uelman, P.J. et al. (1995) *J. Biol. Chem.* 270, 26192–26201. (Exhibit 5).
Meiner, V.M. et al. (1996) *Proc. Natl. Acad. Sci, USA* 93, 14041–14046. (Exhibit 6).
Yang, H. et al. (1997) *J. Biol. Chem.* 272, 3980–3985. (Exhibit 7).
Chang, C.C. et al. (1994) *Somatic Cell Mol. Genet.* 20, 71–74. (Exhibit 8).
Matsuda, H. et al. (1996) *Biochim. Biophys. Acta* 1301, 76–84. (Exhibit 9).
Tavani, D.M. et al. (1982) *J. Lipid Res.* 23, 774–781.(Exhibit 10).
Billheimer, J.T. et al. (1990) *J. Biol. Chem.* 265, 8632–8635. (Exhibit 11).

*Primary Examiner*—Rebecca E. Prouty
*Assistant Examiner*—Richard Hutson
*Attorney, Agent, or Firm*—John P. White; Cooper & Dunham LLP

[57] ABSTRACT

This invention provides an isolated nucleic acid which encodes a diacylglycerol acyltransferase (DGAT); a vector comprising the isolated nucleic acid which encodes a diacylglycerol acyltransferase (DGAT); and a purified polypeptide which is a diacylglycerol acyltransferase. This invention also provides an in vitro method of detecting a diacylglycerol acyltransferase binding site of an enzyme. This invention provides a method for determining whether a subject known to have an imbalance in trigliceride has the imbalance due to a defect in esterification of diacylglycerol to produce triglyceride. This invention also provides a method for treating a subject who has an imbalance in triglyceride levels due to a defect in esterification of diglycerol which comprises introducing the isolated nucleic acid which encodes a diacylglycerol acyltransferase (DGAT) into the subject under conditions such that the nucleic acid expresses a wildtype diacylglycerol acyltransferase, so as to thereby treat the subject. This invention further provides a method for inhibiting wildtype diacylglycerol acyltransferase in a subject which comprises transforming appropriate cells from the subject with a vector which expresses the nucleic acid which encodes a diacylglycerol acyltransferase (DGAT).

14 Claims, 9 Drawing Sheets

Nucleotide (coding and noncoding)

```
GAATGGACGAGAGAGGCGGCCGTCCATTAGTTAGCGGCTCCGGAGCAA
CGCAGCCGTTGTCCTTGAGGCCGACGGGCCTG
ACGCGGGCGGGTTGAACGCGCTGGTGAGGCGGTCACCCGGGCTACGGCG
GCCGGCAGGGGGCAGTGGCGGCCGTTGTCTA
GGGCCCGGAGGTGGGGCCGCGCGCCTCGGGCGCTACGAACCCGGCAGGC
CCACGCTTGGCTGCGGCCGGGTGCGGGCTGA
GGCCATGGGCGACCGCGGCAGCTCCCGGCGCCGGAGGACAGGGTCGCGG
CCCTCGAGCCACGGCGGCGGCGGGCCTGCGG
CGGCGGAAGAAGAGGTGCGGGACGCCGCTGCGGGCCCCGACGTGGGAGC
CGCGGGGGACGCGCCAGCCCCGGCCCCAAC
AAGGACGGAGACGCCGGCGTGGGCAGCGGCCACTGGGAGCTGAGGTGC
CATCGCCTGCAGGATTCTTTATTCAGCTCTGA
CAGTGGCTTCAGCAACTACCGTGGCATCCTGAACTGGTGTGTGGTGATG
CTGATCTTGAGCAATGCCCGGTTATTTCTGG
AGAACCTCATCAAGTATGGCATCCTGGTGGACCCCATCCAGGTGGTTTC
TCTGTTCCTGAAGGATCCCCATAGCTGGCCC
GCCCCATGCCTGGTTATTGCGGCCAATGTCTTTGCTGTGGCTGCATTCCA
GGTTGAGAAGCGCCTGGCGGTGGGTGCCCT
GACGGAGCAGGCGGGACTGCTGCTGCACGTAGCCAACCTGGCCACCATT
CTGTGTTTCCCAGCGGCTGTGGTCTTACTGG
TTGAGTCTATCACTCCAGTGGGCTCCCTGCTGGCGCTGATGGCGCACACC
ATCCTCTTCCTCAAGCTCTTCTCCTACCGC
GACGTCAACTCATGGTGCCGCAGGGCCAGGGCCAAGGCTGCCTCTGCAG
GGAAGAAGGCCAGCAGTGCTGCTGCCCCGCA
CACCGTGAGCTACCCGGACAATCTGACCTACCGCGATCTCTACTACTTCC
TCTTCGCCCCCACCTTGTGCTACGAGCTCA
ACTTTCCCCGCTCTCCCCGCATCCGGAAGCGCTTTCTGCTGCGACGGATCC
TTGAGATGCTGTTCTTCACCCAGCTCCAG
GTGGGGCTGATCCAGCAGTGGATGGTCCCCACCATCCAGAACTCCATGA
AGCCCTTCAAGGACATGGACTACTCACGCAT
CATCGAGCGCCTCCTGAAGCTGGCGGTCCCCAATCACCTCATCTGGCTCA
TCTTCTTCTACTGGCTCTTCCACTCCTGCC
TGAATGCCGTGGCTGAGCTCATGCAGTTTGGAGACCGGGAGTTCTACCG
GGACTGGTGGAACTCCGAGTCTGTCACCTAC
TTCTGGCAGAACTGGAACATCCCTGTGCACAAGTGGTGCATCAGACACT
TCTACAAGCCCATGCTTCGACGGGGCAGCAG
CAAGTGGATGGCCAGGACAGGGGTGTTCCTGGCCTCGGCTTTCTTCCACG
AGTACCTGGTGAGCGTCCCTCTGCGAATGT
TCCGCCTCTGGGCTTTCACGGGCATGATGGCTCAGATCCCACTGGCCTGG
TTCGTGGGCCGCTTTTCCAGGGCAACTAT
GGCAACGCAGCTGTGTGGCTGTCGCTCATCATCGGACAGCCAATAGCCG
TCCTCATGTACGTCCACGACTACTACGTGCT
CAACTATGAGGCCCCAGCGGCAGAGGCCTGAGCTGCACCTGAGGGCCTG
GCTTCTCACTGCCACCTCAAACCCGCTGCCA
GAGCCCACCTCTCCTCCTAGGCCTCGAGTGCTGGGGATGGGCCTGGCTGC
ACAGCATCCTCCTCTGGTCCCAGGGAGGCC
TCTCTGCCCTATGGGGCTCTGTCCTGCACCCCTCAGGGATGGCGACAGCA
GGCCAGACACAGTCTGATGCCAGCTGGGAG
TCTTGCTGACCCTGCCCCGGGTCCGAGGGTGTCAATAAAGTGCTGTCCAG
TGGGAG
```

DNA (coding and noncoding)

AGAAGAGGCAACACGGGCAAGGGCTGCCTGCTGCCCGCTGGAGACCGC
ACCATGGAGCCAGGCGGGGCCCGTCTGCGTCT
GCAGAGGACAGAAGGGCTGGGAGGGGAGCGGGAGCGCCAACCCTGTGG
AGATGGAAACACTGAGACGCACAGAGCCCCGG
ACTTGGTACAATGGACCCGACACATGGAGGCTGTGAAGGCACAATTGC
TGGAGCAAGCGCAGGGACAACTGAGGGAGCTG
CTGGATCGGGCCATGCGGGAGGCTATACAATCcTACCCATCACAAGACA
AACcTCTGCCCCCACCTCCCCCAGGTTCCTT
GAGCAGGACCCAGGAGCCATCCCTGGGGAAACAGAAAGTTTTCATCAT
CCGCAAGTCCCTGCTTGATGAGCTGATGGAGG
TGCAGCATTTCCGCACCATCTACCACATGTTCATCGCTGGCCTGTGTGTC
TTCATCATCAGCACCCTGGCCATCGACTTC
ATTGATGAGGGCAGGCTGCTGCTGGAGTTTGACCTACTGATCTTCAGCT
TCGGACAGCTGCCATTGGCGCTGGTGACCTG
GGTGCCCATGTTTCTGTCCACCCTGTTGGCGCCGTACCAGGCCCTACGGCT
GTGGGCCAGGGGCACCTGGACGCAGGCGA
CGGGCCTGGGCTGTGCGCTGCTAGCCGCCCACGCCGTGGTGCTCTGCGCGC
TGCCGGTCCACGTGGCCGTGGAGCATCAG
CTCCCGCCGGCCTCCCGTTGTGTCCTGGTCTTCGAGCAGGTTAGGTTCCTG
ATGAAAAGCTACTCCTTCCTGAGAGAGGC
TGTGCCTGGGACCCTTCGTGCCAGACGAGGTGAGGGGATCCAGGCCCCC
AGTTTCTCCAGCTACCTCTACTTCCTCTTCT
GCCCAACACTCATCTACAGGGAGACTTACCCTAGGACGCCCTATGTCAG
GTGGAATTATGTGGCCAAGAACTTTGCCCAG
GCCCTGGGATGTGTGCTCTATGCCTGCTTCATCCTGGGCCGCCTCTGTGTT
CCTGTCTTTGCCAACATGAGCCGAGAGCC
CTTCAGCACCCGTGCCCTGGTGCTCTCTATCCTGCATGCCACGTTGCCAGG
CATCTTCATGCTGCTGCTCATCTTCTTTG
CCTTCCTCCATTGCTGGCTCAACGCCTTTGCCGAGATGCTACGATTTGGA
GACAGGATGTTCTACCGGGACTGGTGGAAC
TCAACGTCCTTCTCCAACTACTACCGCACTTGGAACGTGGTGGTCCATGA
CTGGCTGTACAGCTACGTGTATCAGGATGG
GCTGCGGCTCCTTGGTGCCCGGGCCCGAGGGGTAGCCATGCTGGGTGTGT
TCCTGGTcTCCGCAGTGGCCCAtGAGTATA
TCTTCTGCTTCGTCCTGGGGTTCTTCTATCCCGTCATGCTGATACTCTTCC
TTGTCATTGGAGGAATGTTGAAcTTCATG
ATGCATGACCAGCGCACCGGCCCGGCATGGAACGTGCTGATGTGGACCA
TGCTGTTTcTAGGCCAGGGAATCCAGGTCAG
CCTGTACTGCCAGGAGTGGTACGCACGGCGGCACTGCCCCTTACCCCAGG
CAACTTTCTGGGGGCTGGTGACACcTCGAT
cTTGGTCCTGCCATACCTAGAGGTCGGGACAGACGACGCTACCTGCCCAG
ACACCACCAAGTTCTCTGCCTGCAAAACCT
GGGGACCAGGACTCCCTGTCTGCATTCCCCAAATTTGGCTCTGAGTCGAG
GCAACCTGCACACAAGACCCCACCCAAGG
AATGTGCAAGGACTGAGATCTGCAGACTTGTGGGTAACTGATCACAGA
CCTCAGCATGGGGGTGACCAGGGTGACTCTTC
AATCCCTATCCCCATGGGCTGGGTACAGGATATCCTCCTACCCCATGACT
GTCTTAGGGAGACTTGGGGTACCTTATGGA
TTTGATGAATGTGGGGGAACTCAGAGGAACTGGGGCCACCAAGGTTGG
AAAAGGGTTTGGTTCTTGACTTTGTATTCCTT
CCAATACAGCAATAAACTTTGTCTCCCTTTTTATTCATTC

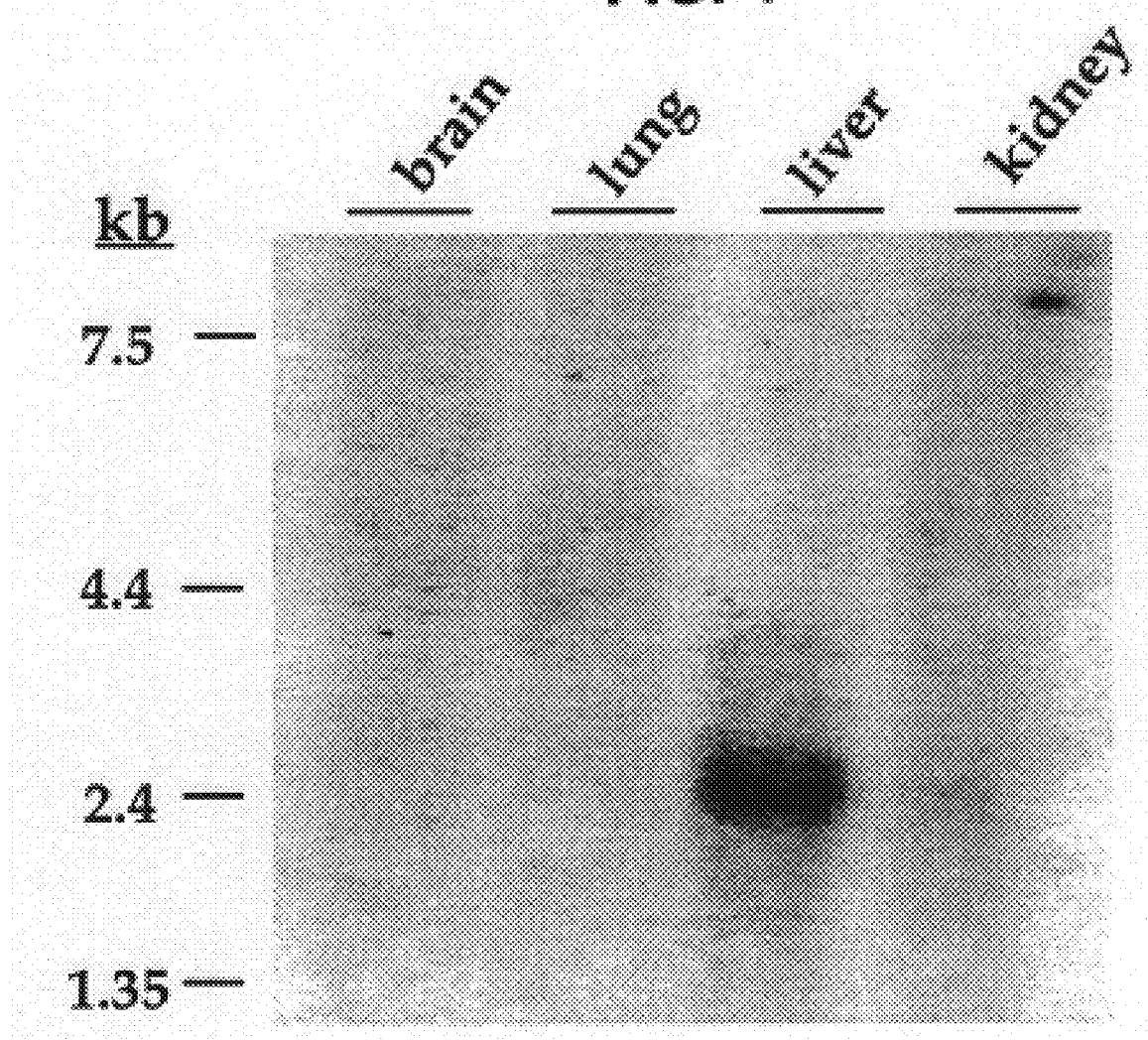

FIG. 7A   The "DWWN" region of the ACAT gene family

```
ARE1    482     ELtRFaDRyF  YgDWWNCvSf  eeFsRiwNVP  VHKfllRHVY  hssmgal.hl  sKS
ARE2    514     ELtRFGDRyF  YgDWWNCvSw  adFsRiwNiP  VHKfllRHVY  hssmssf.kl  nKS
ACAT1   394     EmlRFGDRmF  YkDWWNStSy  snyyRtWNVv  VHdWLyyyaY  kdfLwffskr  fKS
ACAT2   368     EmlRFGDRmF  YrDWWNStSf  snyyRtWNVv  VHdWLysyVY  qdgLrllgar  arg
ARGP1   351     ELmqFGDReF  YrDWWNSeSv  tyFwqnWNiP  VHKWciRHfy  kpmLrrgss.  .Kw
                                π                          *        *

Consensus       EL-RFGDR-F  Y-DWWNS-S-  --F-R-WNVP  VHKWL-RHVY  ---L----  -KS
```

FIG. 7B   The "HSF" region of the ACAT gene family

```
ARE1    306     FvMKSHSFAf  yNgyLWdIkq
ARE2    335     lLMKmHSFAf  yNgyLWgIke
ACAT1   265     FvMKaHSFvr  eNvprvLnsA
ACAT2   240     FLMKSySFlr  eavpgtL.rA
ARGP1   206     FL.KlfSyrd  vNswcr..rA
                    σ

Consensus       FLMKSHSFA-  -N--LWLI-A
```

ISOLATION OF A GENE ENCODING DIACYLGLYCEROL ACYLTRANSFERASE

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

BACKGROUND OF THE INVENTION

The enzyme acyl Coenzyme A-cholesterol acyltransferase 1 (ACAT1) mediates sterol esterification, a crucial component of intracellular lipid homeostasis. Two enzymes catalyze this activity in Saccharomyces cerevisiae (yeast), and several lines of evidence suggest multigene families may also exist in mammals. Using the human ACAT1 sequence to screen databases of expressed sequence tags, we identified two novel and distinct partial human cDNAs. Full length cDNA clones for these ACAT Related Gene Products (ARGP) 1 and 2 were isolated from a hepatocyte (HepG2) cDNA library. ARGP1 was expressed in numerous human adult tissues and tissue culture cell lines, whereas expression of ARGP2 was more restricted. In vitro microsomal assays in a yeast strain deleted for both esterification genes and completely deficient in sterol esterification indicated that ARGP2 esterified cholesterol while ARGP1 did not. In contrast to ACAT1 and similar to liver esterification, the activity of ARGP2 was relatively resistant to a histidine active site modifier. ARGP2 is therefore a tissue specific sterol esterification enzyme which we thus designated ACAT2. We speculate that ARGP1 participates in the Coenzyme A-dependent acylation of substrate(s) other than cholesterol. Consistent with this hypothesis, ARGP1, unlike any other member of this multigene family, possesses a predicted diacylglycerol binding motif suggesting that it may perform the last acylation in triglyceride biosynthesis.

The intracellular formation of sterol esters from fatty acid and sterol is mediated by acyl-CoA cholesterol acyl transferase (ACAT). The pathological accumulation of cholesterol esters in atherosclerotic lesions has lead to intense pursuit of ACAT inhibitors as pharmacological agents. Microsomal ACAT preparations from various tissues display differential sensitivities to some of these agents including histidine (1) modifiers (2). This suggests that more than one protein mediates the esterification reaction, such as occurs in yeast (reviewed in FIG. 3]. Saccharomyces cerevisiae (budding yeast) has two ACAT related enzymes, Are1 and Are2, which are derived from separate genes and have been shown to independently esterify sterols (4,5). In terms of contribution to the sterol ester mass of the cell, Are1 is the minor isoform relative to Are2. These genes were identified based on sequence conservation to a human gene, ACAT1, which encodes an ACAT enzyme with homologs in many mammalian species . The human ACAT1 gene encodes a 550-amino acid polypeptide and is expressed in most tissues, predominantly placenta, lung, kidney, and pancreas (6). ACAT1 has been predicted to have two transmembrane domains (6) and has been immunolocalized to the endoplasmic reticulum (8,9). When murine ACAT1 was disrupted in induced mutant mice, homozygotes for the deletion were found to essentially lack ACAT activity in embryonic fibroblasts and have negligible amounts of cholesterol ester in the adrenal cortex and peritoneal macrophages (10). However, cholesterol ester accumulation was normal in hepatocytes while dietary cholesterol absorption, an indirect marker for intestinal cholesterol esterification, was indistinguishable from control litter mates. This is consistent with the concept of a multigene family for this activity.

ACAT isoenzymes may be required to perform the variety of physiological roles mediated by cholesterol esterification. Increases in cellular free cholesterol above certain levels are cytotoxic and are ameliorated by cholesterol ester formation (11). In hepatocytes, the bulk of cholesterol secreted in very low density lipoprotein (VLDL) is esterified intracellularly and determines apolipoprotein B secretion rates. Cholesterol esterification in the enterocyte may be necessary for cholesterol absorption from the lumen and secretion in chylomicrons into the lymph (15). The formation of cholesterol ester stores could also provide a readily available substrate for steroid hormone synthesis in steroidogenic tissues (16, 17). It is likely that different ACAT isozymes mediate each of these processes, and the data presented here support that hypothesis.

We reasoned that additional human ACAT proteins would have sequence similarity to regions conserved between human ACAT1 and yeast Are1 and Are2 (4). Accordingly, an ACAT consensus sequence was used to screen the data base of expressed sequence tags (dbEST). Several cDNA entries were identified which were transcribed from two independent human genes. This study is a description of the isolation of full-length cDNA clones for two ACAT related gene products (ARGP1 and ARGP2), examination of their pattern of tissue expression, and assays of enzymatic activity. We show that ARGP2 can catalyze the formation of sterol ester from cholesterol and oleoyl-CoA, leading us to rename this gene, ACAT2. By contrast, ARGP1 did not detectably esterify cholesterol and we propose that it performs acyl-CoA dependent acylation of other molecules, such as diacylglycerol.

SUMMARY OF THE INVENTION

This invention provides an isolated nucleic acid which encodes a diacylglycerol acyltransferase (DGAT).

This invention provides a vector comprising the isolated nucleic acid which encodes a diacylglycerol acyltransferase (DGAT).

This invention provides a method of obtaining a polypeptide in purified form which comprises: (a) introducing the vector comprising the isolated nucleic acid which encodes a diacylglycerol acyltransferase (DGAT) into a suitable host cell; (b) culturing the resulting cell so as to produce the polypeptide; (c) recovering the polypeptide produced in step (b); and (d) purifying the polypeptide so recovered.

This invention provides a purified polypeptide which is a diacylglycerol acyltransferase.

This invention provides an oligonucleotide of at least 15 nucleotides capable of specifically hybridizing with a unique sequence of nucleotides present within a nucleic acid which encodes a diacylglycerol acyltransferase.

This invention provides a nucleic acid having a sequence complementary to the sequence of the isolated nucleic acid which encodes a diacylglycerol acyltransferase (DGAT).

This invention provides an in vitro method of detecting a diacylglycerol acyltransferase binding site of an enzyme comprising: (a) contacting a nucleic acid molecule encoding an enzyme with an oligonucleotide of at least 15 nucleotides capable of specifically hybridizing with a unique sequence of nucleotides present within a nucleic acid which encodes a diacylglycerol acyltransferase; and (b) detecting the nucleic acid molecule in step (a) which have hybridized to the oligonucleotide of at least 15 nucleotides capable of specifically hybridizing with a unique sequence of nucleotides present within a nucleic acid which encodes a diacylglycerol acyltransferase, detection of hybridization indicating that the enzyme has a diacylglycerol acyltransferase binding site.

This invention provides a method for determining whether a subject known to have an imbalance in triglyceride has the imbalance due to a defect in esterification of diacylglycerol to produce triglyceride which comprises: (a) obtaining from the subject a nucleic acid sample; and (b) determining whether any nucleic acid in the sample from step (a) is, or is derived from, a nucleic acid which encodes a mutant diacylglycerol acyltransferase so as to thereby determine whether the subject's imbalance in triglyceride levels is due to a defect in esterification of diacylglycerol.

This invention provides a method for treating a subject who has an imbalance in triglyceride levels due to a defect in esterification of diglycerol which comprises introducing the isolated nucleic acid which encodes a diacylglycerol acyltransferase (DGAT) into the subject under conditions such that the nucleic acid expresses a wildtype diacylglycerol acyltransferase, so as to thereby treat the subject.

This invention provides a method for inhibiting wildtype diacylglycerol acyltransferase in a subject which comprises transforming appropriate cells from the subject with a vector which expresses the nucleic acid which encodes a diacylglycerol acyltransferase (DGAT), and introducing the transformed cells into the subject so as to thereby inhibit wildtype diacylglycerol acyltransferase.

This invention provides a method for inhibiting the wildtype diacylglycerol acyltransferase in a subject which comprises introducing the any of the above-described oligonucleotides of at least 15 nucleotides capable of specifically hybridizing with a unique sequence of nucleotides present within a nucleic acid which encodes a diacylglycerol acyltransferase into the subject so as to thereby inhibit the wildtype diacylglycerol acyltransferase.

This invention provides a method for identifying a chemical compound which is capable of inhibiting diacylglycerol acyltransferase in a subject which comprises: (a) contacting a wildtype diacylglycerol acyltransferase with the chemical compound under conditions permitting binding between the diacylglycerol acyltransferase and the chemical compound; (b) detecting specific binding of the chemical compound to the diacylglycerol acyltransferase; and c) determining whether the chemical compound inhibits the activity of the diacylglycerol acyltransferase so as to identify a chemical compound which is capable of inhibiting diacylglycerol acyltransferase in a subject.

This invention provides a method for identifying a chemical compound which is capable of enhancing diacylglycerol acyltransferase in a subject which comprises: (a) contacting a wildtype diacylglycerol acyltransferase with the chemical compound under conditions permitting binding between the diacylglycerol acyltransferase and the chemical compound; (b) detecting specific binding of the chemical compound to the diacylglycerol acyltransferase; and c) determining whether the chemical compound enhances the activity of the diacylglycerol acyltransferase so as to identify a chemical compound which is capable of enhancing diacylglycerol acyltransferase in a subject.

This invention provides a pharmaceutical composition comprising the chemical compound which is capable of inhibiting diacylglycerol acyltransferase identified by the above-described method in an amount effective to inhibit diacylglycerol acyltransferase in a subject and a pharmaceutically effective carrier.

This invention provides a pharmaceutical composition comprising the chemical compound which is capable of enhancing diacylglycerol acyltransferase activity identified by the above-described method in an amount effective to enhance diacylglycerol acyltransferase activity in the subject and a pharmaceutically effective carrier.

This invention provides a method of treating a subject who has atherosclerosis comprising the pharmaceutical composition comprising the chemical compound which is capable of inhibiting diacylglycerol acyltransferase identified by the above-described method in an amount effective to inhibit diacylglycerol acyltransferase in a subject and a pharmaceutically effective carrier.

This invention provides a method of treating a subject who has hyperlipidemia comprising the pharmaceutical composition comprising the chemical compound which is capable of inhibiting diacylglycerol acyltransferase identified by the above-described method in an amount effective to inhibit diacylglycerol acyltransferase in a subject and a pharmaceutically effective carrier.

This invention provides a method of reducing the deposition of fat cells in a subject by decreasing the amount of triglycerides produced in adipose cells of the subject comprising administering the pharmaceutical composition comprising the chemical compound which is capable of inhibiting diacylglycerol acyltransferase identified by the above-described method in an amount effective to inhibit diacylglycerol acyltransferase in a subject and a pharmaceutically effective carrier.

This invention provides a transgenic, nonhuman mammal comprising the isolated nucleic acid which encodes a diacylglycerol acyltransferase (DGAT).

This invention provides an antibody directed to an epitope of a purified diacylglycerol acyltransferase. This invention provides an antibody capable of specifically binding to a purified diacylglycerol acyltransferase.

This invention furtehr provides an isolated nucleic acid which encodes an acylcoenzyme A: cholesterol acyltransferase related gene product II (ARGP2 or ACAT 2).

This invention provides a vector comprising the isolated nucleic acid which encodes an acylcoenzyme A: cholesterol acyltransferase related gene product II (ARGP2 or ACAT 2).

This invention provides a purified acylcoenzyme A: cholesterol acyltransferase related gene product II (ARGP 2).

This invention provides an oligonucleotide of at least 15 nucleotides capable of specifically hybridizing with a unique sequence of nucleotides present within a nucleic acid which encodes an acylcoenzyme A: cholesterol acyltransferase related gene product II (ARGP 2) diacylglycerol acyltransferase.

This invention provides a nucleic acid having a sequence complementary to the sequence of the isolated nucleic acid which encodes an acylcoenzyme A: cholesterol acyltransferase related gene product II (ARGP2 or ACAT 2).

This invention provides a transgenic, nonhuman mammal comprising the isolated nucleic acid which encodes an acylcoenzyme A: cholesterol acyltransferase related gene product II (ARGP2 or ACAT 2).

This invention provides an antibody directed to an epitope of a purified acylcoenzyme A: cholesterol acyltransferase related gene product II (ARGP 2). This invention provides an antibody capable of specifically binding to a purified acylcoenzyme A: cholesterol acyltransferase related gene product II (ARGP 2).

BRIEF DESCRIPTION OF THE FIGURES

FIGS. 1A and B. ARGP1 predicted peptide sequence. A 1976-bp ARGP1 cDNA clone (SEQ ID NO:2) was identified by colony hybridization screening of a HepG2 cDNA library. Translation of this clone predicts the 488 amino acid peptide shown (SEQ ID NO:1). The residues in bold are conserved with human ACAT1. The underlined portions are predicted transmembrane domains, a potential N-linked glycosylation site is boxed and a putative tyrosine phosphorylation motif is in brackets. The sequence has been deposited at GenBank, accession # AF059202.

FIGS. 2A and B. ARGP2 predicted peptide sequence. A 2040-bp ARGP2 cDNA (SEQ ID NO:4) isolated by screening a HepG2 cDNA predicts the 522 amino acid polypeptide shown (SEQ ID NO:3). The residues in bold are conserved with human ACAT1. The underlined portions are predicted transmembrane domains, two potential N-linked glycosylation sites are boxed, a putative tyrosine phosphorylation motif is in brackets, and the circles mark the leucine zipper heptad motif. The sequence has been deposited at GenBank, accession # AF059203.

FIG. 4. Northern Blot analysis of ARGP2 expression in human fetal tissues. 2 µg of mRNA from human fetal tissues (Clontech Fetal MTN II) was resolved on a denaturing, 1.2% agarose gel, transferred to a nylon membrane, and hybridized with a [$^{32}$P]dCTP, random-hexamer labeled, human ARGP2 probe in Express Hyb solution for 1 hour at 65° C. After washing in 0.2× SSC, 0.1% SDS at 68° C. for 40 minutes, the membranes were exposed to X-ray film. Molecular weight markers were as supplied by Clontech.

FIGS. 7A and B. Consensus Sequences in the ACAT Multigene Family. Two regions of structural and functional conservation are shown. The amino acid position of each initial residue is shown. Upper case residues indicate those of the consensus calculated with a plurality of 2. A. The DWWN region (SEQ ID NO:5–SEQ ID NO:10). The FY.D-WWN motif is invariant in all members identified to date of this gene family, the tyrosine and tryptophans being critical to activity (Guo et al in preparation). In all but ARGP1, the Tyr constitutes a candidate target for phosphorylation (indicated in bold and by π). In ARGP1, the underlined sequence HKWCIRHFYKP represents a candidate for diacylglycerol binding as found in protein kinase C and diacylglycerol kinases (motif, H . . . [FWY] . . . [KR] . . . F . . . P). The asterisks identify those residues critical to definition of this motif that distinguish ARGP1 from the other members of the family. B. The HSF region (SEQ ID NO:11–SEQ ID NO:16). The central serine residue (indicated θ) was found to be critical to the activity and stability of chinese hamster ovary

DETAILED DESCRIPTION OF THE INVENTION

Figures 3A, 3B:
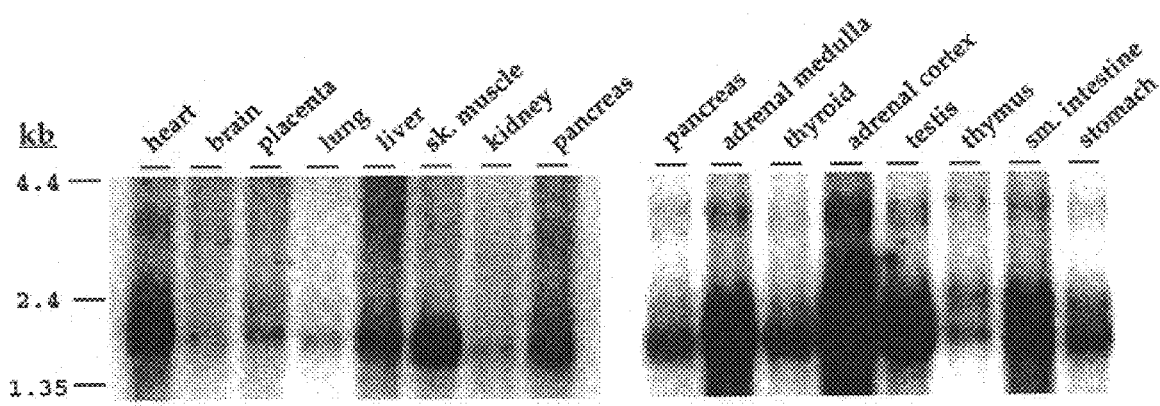
FIGS. 3A and B. Northern Blot analysis of ARGP1 expression in human adult tissues. 2 µg of mRNA from human adult tissues (panel A, Clontech MTN I and panel B, Endocrine system MTN) was hybridized with a [$^{32}$P]dCTP, random-hexamer labeled, human ARGP1 probe in Express Hyb solution for 1 hour at 68° C. After washing in 0.2× SSC, 0.1% SDS at 60° C. for 40 minutes, the membranes were exposed to X-ray film. Molecular weight markers were as supplied by Clontech.

The following standard abbreviations are used throughout the specification to indicate specific nucleotides:

C=cytosine A=adenosine

T=thymidine G=guanosine

Figure 1A:
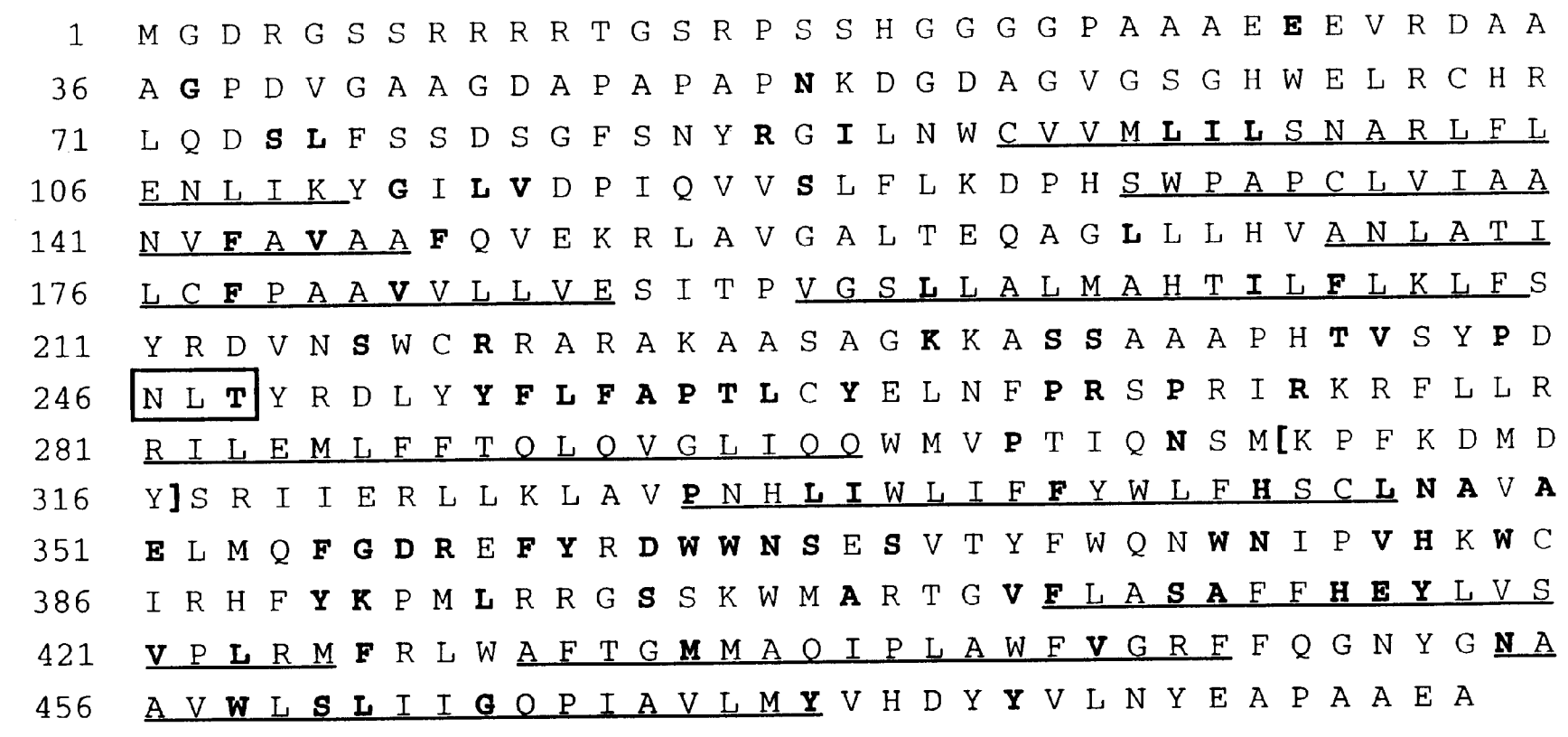

This invention provides an isolated nucleic acid which encodes a diacylglycerol acyltransferase (DGAT). In an embodiment the above-described isolated nucleic acid is DNA or RNA. In another embodiment the isolated nucleic acid is cDNA or genomic DNA. In a further embodiment the encoded diacylglycerol acyltransferase has substantially the same amino acid as set forth in FIG. 1. In a still further embodiment nucleic acid encodes a human diacylglycerol acyltransferase. In another embodiment the above-described isolated nucleic acid has a nucleic acid sequence as set forth in FIG. 1.

The DNA molecules of the subject invention also include DNA molecules coding for polypeptide analogs, fragments or derivatives of antigenic polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs where in one or more amino acid residues is added to a terminal or medial portion of the polypeptides) and which share some or all properties of naturally-occurring forms. These molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

The DNA molecules described and claimed herein are useful for the information which they provide concerning the amino acid sequence of the polypeptides, diacylglycerol acyltransferase (DGAT) and acylcoenzyme A: cholesterol acyltransferase related gene product II (ARGP2 or ACAT 2), and as products for the large scale synthesis of the polypeptides (diacylglycerol acyltransferase (DGAT) and acylcoenzyme A: cholesterol acyltransferase related gene product II (ARGP2 or ACAT 2)) or fragments thereof), portions which are involved in protein-protein interactions) by a variety of recombinant techniques. The molecule is useful for generating new cloning and expression vectors, transformed and transfected prokaryotic and eukaryotic host cells, and new and useful methods for cultured growth of such host cells capable of expression of the polypeptides (diacylglycerol acyltransferase (DGAT) and acylcoenzyme A: cholesterol acyltransferase related gene product II (ARGP2 or ACAT 2) or portions thereof and related products.

This invention provides a vector comprising the isolated nucleic acid which encodes a diacylglycerol acyltransferase (DGAT). In an embodiment the vector further comprises a promoter of RNA transcription operatively linked to the nucleic acid. In another embodiment of the above-described vectors the promoter comprises a bacterial, yeast, insect or mammalian promoter. In an embodiment the vectors may further comprise a plasmid, cosmid, yeast artificial chromosome (YAC), bacteriophage or eukaryotic viral DNA.

This invention provides a host vector system for the production of a polypeptide which comprises any of the the above-described vectors in a suitable host. In an embodiment of the host vector system the suitable host is a prokaryotic or eukaryotic cell. In another embodiment of the host vector system the prokaryotic cell is a bacterial cell. In a further embodiment of the host vector system the eukaryotic cell is a yeast, insect, plant or mammalian cell.

Numerous vectors for expressing the inventive proteins may be employed. Such vectors, including plasmid vectors, cosmid vectors, bacteriophage vectors and other viruses, are well known in the art. For example, one class of vectors utilizes DNA elements which are derived from animal viruses such as bovine papilloma virus, polyoma virus, adenovirus, vaccinia virus, baculovirus, retroviruses (RSV, MMTV or MoMLV), Semliki Forest virus or SV40 virus. Additionally, cells which have stably integrated the DNA into their chromosomes may be selected by introducing one or more markers which allow for the selection of transfected host cells. The markers may provide, for example, prototrophy to an auxotrophic host, biocide resistance or resistance to heavy metals such as copper. The selectable marker gene can be either directly linked to the DNA sequences to be expressed, or introduced into the same cell by cotransformation.

Regulatory elements required for expression include promoter sequences to bind RNA polymerase and transcription initiation sequences for ribosome binding. Additional elements may also be needed for optimal synthesis of mRNA. These additional elements may include splice signals, as well as enhancers and termination signals. For example, a bacterial expression vector includes a promoter such as the lac promoter and for transcription initiation the Shine-Dalgarno sequence and the start codon AUG. Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well known in the art, for example the methods described above for constructing vectors in general.

These vectors may be introduced into a suitable host cell to form a host vector system for producing the inventive proteins. Methods of making host vector systems are well known to those skilled in the art.

Suitable host cells include, but are not limited to, bacterial cells (including gram positive cells), yeast cells, fungal cells, insect cells and animal cells. Suitable animal cells include, but are not limited to HeLa cells, Cos cells, CV1 cells and various primary mammalian cells. Numerous mammalian cells may be used as hosts, including, but not limited to, the mouse fibroblast cell NIH-3T3 cells, CHO cells, HeLa cells, Ltk$^-$ cells and COS cells. Mammalian cells may be transfected by methods well known in the art such as calcium phosphate precipitation, electroporation and microinjection.

One of ordinary skill in the art will easily obtain unique sequences from the cDNA cloned in plasmids. Such unique sequences may be used as probes to screen various mammalian cDNA libraries and genomic DNAs, e.g. mouse, rat and bovine, to obtain homologous nucleic acid sequences and to screen different cDNA tissue libraries to obtain isoforms of the obtained nucleic acid sequences. Nucleic acid probes from the cDNA cloned in plasmids may further be used to screen other human tissue cDNA libraries to obtain isoforms of the nucleic acid sequences encoding (diacylglycerol acyltransferase (DGAT) or acylcoenzyme A: cholesterol acyltransferase related gene product II (ARGP2 or ACAT 2) (as well as to screen human genomic DNA to obtain the analogous nucleic acid sequences. The homologous nucleic acid sequences and isoforms may be used to produce the proteins encoded thereby.

This invention provides a method for producing a polypeptide which comprises growing any of the above-described host vector systems comprising the isolated nucleic acid which encodes a diacylglycerol acyltransferase (DGAT) under suitable conditions permitting production of the polypeptide and recovering the polypeptide so produced.

This invention provides a method of obtaining a polypeptide in purified form which comprises: (a) introducing the vector comprising the isolated nucleic acid which encodes a diacylglycerol acyltransferase (DGAT) into a suitable host cell; (b) culturing the resulting cell so as to produce the polypeptide; (c) recovering the polypeptide produced in step (b); and (d) purifying the polypeptide so recovered.

This invention provides a purified polypeptide which is a diacylglycerol acyltransferase. This diacylglycerol acyltransferase may also catalyze retinol esterification, methyl ester esterification, triterpine esterification, and use monoacylglycerol transferase as a substrate. In an embodiment the above-described purified polypeptide has the amino acid sequence set forth in FIG. 1. In an embodiment the purified polypeptide has a diacylglycerol binding motif. In an embodiment of the purified polypeptide the diacylglycerol binding motif is at amino acids 382–392.

This invention provides an oligonucleotide of at least 15 nucleotides capable of specifically hybridizing with a unique sequence of nucleotides present within a nucleic acid which encodes a diacylglycerol acyltransferase. In an embodiment of the oligonucleotide of at least 15 nucleotides capable of specifically hybridizing with a unique sequence of nucleotides present within a nucleic acid which encodes a diacylglycerol acyltransferase, the nucleic acid which encodes a diacylglycerol acyltransferase has the nucleic acid sequence set forth in FIG. 1. In further embodiments of any of the above-described oligonucleotides the nucleic acid may be DNA or RNA.

This invention provides a nucleic acid having a sequence complementary to the sequence of the isolated nucleic acid which encodes a diacylglycerol acyltransferase (DGAT).

This invention provides an in vitro method of detecting a diacylglycerol acyltransferase binding site of an enzyme comprising: (a) contacting a nucleic acid molecule encoding an enzyme with an oligonucleotide of at least 15 nucleotides capable of specifically hybridizing with a unique sequence of nucleotides present within a nucleic acid which encodes a diacylglycerol acyltransferase; and (b) detecting the nucleic acid molecule in step (a) which have hybridized to the oligonucleotide of at least 15 nucleotides capable of specifically hybridizing with a unique sequence of nucleotides present within a nucleic acid which encodes a diacylglycerol acyltransferase, detection of hybridization indicating that the enzyme has a diacylglycerol acyltransferase binding site. Accordingly the above-described method (or modifications thereof which would known to one of ordinary skill in the art) may be used to diagnose a subject having an elevated expression of the nucleic acid encoding a diacylglycerol acyltransferase, measuring the diacylglycerol acyltransferase activity in cells of the subject, or using a mutant of the nucleic acid encoding a diacylglycerol acyltransferase to detect activity of the enzyme which differs from activity of this gene (DGAT) in a normal, i.e. non-diseased state, e.g. by using a liver sample (biopsy) to perform any of the above-envisioned diagnostic assays.

This invention provides a method for determining whether a subject known to have an imbalance in triglyceride has the imbalance due to a defect in esterification of diacylglycerol to produce triglyceride which comprises: (a) obtaining from the subject a nucleic acid sample; and (b) determining whether any nucleic acid in the sample from step (a) is, or is derived from, a nucleic acid which encodes a mutant diacylglycerol acyltransferase so as to thereby determine whether the subject's imbalance in triglyceride levels is due to a defect in esterification of diacylglycerol.

In an embodiment of the above-described method the determining of step (b) comprises: (i) contacting the sample of step (a) with any of the above-described isolated nucleic acids which encode a diacylglycerol acyltransferase (ARGP 1) which is cDNA or genomic DNA or any of the above-described oligonucleotides of at least 15 nucleotides capable of specifically hybridizing with a unique sequence of nucleotides present within a nucleic acid which encodes a diacylglycerol acyltransferase under conditions permitting binding of any nucleic acid in the sample which is, or is derived from, a nucleic acid which encodes a mutant diacylglycerol acyltransferase to the nucleic acid or oligonucleotide so as to form a complex; (ii) isolating the complex so formed; and (iii) identifying the nucleic acid in the isolated complex so as to thereby determine whether any nucleic acid in the sample contains a nucleic acid which is, or is derived from, a nucleic acid which encodes a mutant diacylglycerol acyltransferase. In an embodiment of the above-described method, the isolated nucleic acid or the oligonucleotide is labeled with a detectable marker. In other embodiments the detectable marker is a radioactive isotope, a fluorophor or an enzyme. In further embodiments of the above-described methods the nucleic acid sample is first bound to a solid matrix before performing step (i). In another embodiment of the above-described methods the sample comprises blood or sera.

Alternatively, an imbalance or overproduction of triglycerides may be detected by determining the activity of a gene which regulates or affects the expression of diacylglycerol acyltransferase or activity of this enzyme, i.e. by detecting cahnges in expression of the regukator gene or measuring the product of the regulator gene.

This invention provides a method for treating a subject who has an imbalance in triglyceride levels due to a defect in esterification of diglycerol which comprises introducing the isolated nucleic acid which encodes a diacylglycerol acyltransferase (ARGP 1) into the subject under conditions such that the nucleic acid expresses a wildtype diacylglycerol acyltransferase, so as to thereby treat the subject. In an embodiment the triglyceride levels are elevated, i.e. at a level which exceed the level of triglycerides in a healthy subject. Accordingly, the above-described method for treating a subject who has an imbalance in triglyceride levels may be used to treat hypertriglyceridemia, hyperlipidemia, atherosclerosis, heart disease, obesity or other diseases associated with high or excessive levels of triglyceride.

This invention provides a method for inhibiting wildtype diacylglycerol acyltransferase in a subject which comprises transforming appropriate cells from the subject with a vector which expresses the nucleic acid which encodes a diacylglycerol acyltransferase (DGAT), and introducing the transformed cells into the subject so as to thereby inhibit wildtype diacylglycerol acyltransferase. In an embodiment of the above-described method the nucleic acid is capable of specifically hybridizing to a mRNA molecule encoding wildtype diacylglycerol acyltransferase so as to prevent translation of the mRNA molecule.

This invention provides a method for inhibiting the wildtype diacylglycerol acyltransferase in a subject which comprises introducing the any of the above-described oligonucleotides of at least 15 nucleotides capable of specifically hybridizing with a unique sequence of nucleotides present within a nucleic acid which encodes a diacylglycerol acyltransferase into the subject so as to thereby inhibit the wildtype diacylglycerol acyltransferase. In another embodiment of the above-described method the above-described oligonucleotides are capable of specifically hybridizing to a mRNA molecule encoding diacylglycerol acyltransferase so as to prevent translation of the mRNA molecule.

This invention provides a method for identifying a chemical compound which is capable of inhibiting diacylglycerol acyltransferase in a subject which comprises: (a) contacting a wildtype diacylglycerol acyltransferase with the chemical compound under conditions permitting binding between the diacylglycerol acyltransferase and the chemical compound; (b) detecting specific binding of the chemical compound to the diacylglycerol acyltransferase; and c) determining whether the chemical compound inhibits the activity of the diacylglycerol acyltransferase so as to identify a chemical compound which is capable of inhibiting diacylglycerol acyltransferase in a subject.

This invention provides a method for identifying a chemical compound which is capable of enhancing diacylglycerol acyltransferase in a subject which comprises: (a) contacting a wildtype diacylglycerol acyltransferase with the chemical compound under conditions permitting binding between the diacylglycerol acyltransferase and the chemical compound; (b) detecting specific binding of the chemical compound to the diacylglycerol acyltransferase; and c) determining whether the chemical compound enhances the activity of the diacylglycerol acyltransferase so as to identify a chemical compound which is capable of enhancing diacylglycerol acyltransferase in a subject. As used herein, enhancing diacylglycerol acyltransferase in a subject is defined as elevating the activity of the enzyme in the subject.

This invention provides a pharmaceutical composition comprising the chemical compound which is capable of inhibiting diacylglycerol acyltransferase identified by the above-described method in an amount effective to inhibit diacylglycerol acyltransferase in a subject and a pharmaceutically effective carrier.

This invention provides a pharmaceutical composition comprising the chemical compound which is capable of enhancing diacylglycerol acyltransferase activity identified by the above-described method in an amount effective to enhance diacylglycerol acyltransferase activity in the subject and a pharmaceutically effective carrier.

This invention provides a method of treating a subject who has atherosclerosis comprising the pharmaceutical composition comprising the chemical compound which is capable of inhibiting diacylglycerol acyltransferase identified by the above-described method in an amount effective to inhibit diacylglycerol acyltransferase in a subject and a pharmaceutically effective carrier.

This invention provides a method of treating a subject who has hyperlipidemia comprising the pharmaceutical composition comprising the chemical compound which is capable of inhibiting diacylglycerol acyltransferase identified by the above-described method in an amount effective to inhibit diacylglycerol acyltransferase in a subject and a pharmaceutically effective carrier. The above-described method may be used to treat subjects having diseases which include but are not limitred to hypertriglyceridemia, heart disease, obesity or other diseases assocaited with levels of triglycerides at a level above the level found in healthy subjects.

This invention provides a method of reducing the deposition of fat cells in a subject by decreasing the amount of triglycerides produced in adipose cells of the subject comprising administering the pharmaceutical composition comprising the chemical compound which is capable of inhibiting diacylglycerol acyltransferase identified by the above-described method in an amount effective to inhibit diacylglycerol acyltransferase in a subject and a pharmaceutically effective carrier. Triglyceride levels may also be decreased in the liver of a subject having any disease associated with elevated triglyceride levels, i.e. higher than the levels found in healthy subjects. Accordingly, the administration of the above-described inhibitor(s) would decrease the triglyceride levels in the serum of the subject.

This invention provides a transgenic, nonhuman mammal comprising the isolated nucleic acid which encodes a diacylglycerol acyltransferase (DGAT).

This invention provides an antibody directed to an epitope of a purified diacylglycerol acyltransferase. This invention provides an antibody capable of specifically binding to a purified diacylglycerol acyltransferase. In further embodiments of the above-described antibodies the diacylglycerol acyltransferase is a human diacylglycerol acyltransferase. In still further embodiments of the above-described antibodies the antibodies may be a polyclonal antibody or a monoclonal antibody. In other embodiments the polyclonal antibodies or a monoclonal antibodies directed to an epitope of a purified diacylglycerol acyltransferase, wherein the epitope is the diacylglycerol acyltransferase binding site of the enzyme.

Polyclonal antibodies may be produced by injecting a host animal such as rabbit, rat, goat, mouse or other animal with the immunogen(s) of this invention, e.g. a purified human DGAT or a purified human ARGP2 (ACAT 2), described infra. The sera are extracted from the host animal and are screened to obtain polyclonal antibodies which are specific to the immunogen. Methods of screening for polyclonal antibodies are well known to those of ordinary skill in the art such as those disclosed in Harlow & Lane, *Antibodies: A Laboratory Manual*, (Cold Spring Harbor Laboratories, Cold Spring Harbor, N.Y.: 1988) the contents of which are hereby incorporated by reference.

The monoclonal antibodies may be produced by immunizing for example, mice with an immunogen (the polypeptides or fragments thereof as described herein). The mice are inoculated intraperitoneally with an immunogenic amount of the above-described immunogen and then boosted with similar amounts of the immunogen. Spleens are collected from the immunized mice a few days after the final boost and a cell suspension is prepared from the spleens for use in the fusion.

Hybridomas may be prepared from the splenocytes and a murine tumor partner using the general somatic cell hybridization technique of Kohler, B. and Milstein, C., Nature (1975) 256:495–497. Available murine myeloma lines, such as those from the American Type Culture Collection (ATCC) 12301 Parklawn Drive, Rockville, Md. 20852 USA, may be used in the hybridization. Basically, the technique involves fusing the tumor cells and splenocytes using a fusogen such as polyethylene glycol. After the fusion the cells are separated from the fusion medium and grown in a selective growth medium, such as HAT medium, to eliminate unhybridized parent cells. The hybridomas may be expanded, if desired, and supernatants may be assayed by conventional immunoassay procedures, for example radioimmunoassay, using the immunizing agent as antigen. Positive clones may be characterized further to determine whether they meet the criteria of the invention antibodies.

Hybridomas that produce such antibodies may be grown in vitro or in vivo using known procedures. The monoclonal antibodies may be isolated from the culture media or body fluids, as the case may be, by conventional immunoglobulin purification procedures such as ammonium sulfate precipitation, gel electrophoresis, dialysis, chromatography, and ultrafiltration, if desired.

In the practice of the subject invention any of the above-described antibodies may be labeled with a detectable marker. In one embodiment, the labeled antibody is a purified labeled antibody. The term "antibody" includes, by way of example, both naturally occurring and non-naturally occurring antibodies. Specifically, the term "antibody" includes polyclonal and monoclonal antibodies, and fragments thereof. Furthermore, the term "antibody" includes chimeric antibodies and wholly synthetic antibodies, and fragments thereof. A "detectable moiety" which functions as detectable labels are well known to those of ordinary skill in the art and include, but are not limited to, a fluorescent label, a radioactive atom, a paramagnetic ion, biotin, a chemiluminescent label or a label which may be detected through a secondary enzymatic or binding step. The secondary enzymatic or binding step may comprise the use of digoxigenin, alkaline phosphatase, horseradish peroxidase, β-galactosidase, fluorescein or steptavidin/biotin. Methods of labeling antibodies are well known in the art.

This invention provides a pharmaceutical composition comprising an amount of any of the above-desribed oligonucleotides, effective to prevent overexpression of a human diacylglycerol acyltransferase and a pharmaceutically acceptable carrier capable of passing through a cell membrane.

This invention provides a method of administering the pharmaceutical compositions described herein comprising an amount of any of the herein-described oligonucleotides, nucleic acids (e.g. DGAT or ACAT 2), vectors containing said nucleic acids, polypeptides, or antibodies which are determined to be potentially therapeutic, wherein the administration is intravenous, intraperitoneal, intrathecal, intralymphatical, intramuscular, intralesional, parenteral, epidural, subcutaneous; by infusion, liposome-mediated delivery, aerosol delivery; topical, oral, nasal, anal, ocular or otic delivery.

The present invention also provides a pharmaceutical composition comprising a effective amount of any of the herein-described oligonucleotides, nucleic acids (e.g. DGAT or ACAT 2), vectors containing said nucleic acids, polypeptides, or antibodies which are determined to be potentially therapeutic and a pharmaceutically acceptable carrier. In the subject invention an "effective amount" is any amount of the herein-described oligonucleotides, nucleic acids (e.g. DGAT), vectors containing said nucleic acids, polypeptides, or antibodies which are determined to be potentially therapeutic, which, when administered to a subject suffering from a disease or abnormality against which the above-described oligonucleotides, nucleic acids, vectors containing said nucleic acids, or antibodies which are determined to be potentially therapeutic, are effective, causes reduction, remission, or regression of the disease or abnormality. In the practice of this invention the "pharmaceutically acceptable carrier" is any physiological carrier known to those of ordinary skill in the art useful in formulating pharmaceutical compositions.

In one preferred embodiment the pharmaceutical carrier may be a liquid and the pharmaceutical composition would be in the form of a solution. In another equally preferred embodiment, the pharmaceutically acceptable carrier is a solid and the composition is in the form of a powder or tablet. In a further embodiment, the pharmaceutical carrier is a gel and the composition is in the form of a suppository or cream. In a further embodiment the compound may be formulated as a part of a pharmaceutically acceptable transdermal patch.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by for example, intramuscular, intrathecal, epidural, intraperitoneal or subcutaneous injection. Sterile solutions can also be administered intravenously. The compounds may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings.

The above-described ligands, oligonucleotides polypeptides, or antibodies which are determined to be potentially therapeutic can be administered orally in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

The above-described oligonucleotides, nucleic acids (e.g. DGAT), vectors containing said nucleic acids, polypeptides, or antibodies which are determined to be potentially therapeutic can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

Optimal dosages to be administered may be determined by those skilled in the art, and will vary with the particular oligonucleotides, nucleic acids (e.g. DGAT), vectors containing said nucleic acids, polypeptides, or antibodies in use, the strength of the preparation, the mode of administration, and the advancement of the disease condition or abnormality. Additional factors depending on the particular subject being treated will result in a need to adjust dosages, including subject age, weight, gender, diet, and time of administration.

This invention further provides an isolated nucleic acid which encodes an acylcoenzyme A: cholesterol acyltransferase related gene product II (ARGP2 or ACAT 2).

In an embodiment of the isolated nucleic acid, the nucleic acid is DNA or RNA. In a further embodiment the nucleic acid is cDNA or genomic DNA. In another embodiment of the isolated nucleic acid the encoded acylcoenzyme A: cholesterol acyltransferase related gene product II as set forth in FIG. 2.

This invention provides a vector comprising the isolated nucleic acid which encodes an acylcoenzyme A: cholesterol acyltransferase related gene product II (ARGP2 or ACAT 2) In an embodiment the vector further comprises a promoter of RNA transcription operatively linked to the nucleic acid. In another embodiment of the vector the promoter comprises a bacterial, yeast, insect or mammalian promoter. In an embodiment the vector further comprises a plasmid, cosmid, yeast artificial chromosome (YAC), bacteriophage or eukaryotic viral DNA.

This invention provides a host vector system for the production of a polypeptide which comprises the above-described vector comprising a promoter of RNA transcription operatively linked to the nucleic acid which encodes an acylcoenzyme A: cholesterol acyltransferase related gene product II (ARGP2 or ACAT 2) in a suitable host. In an embodiment of host vector the suitable host is a prokaryotic or eukaryotic cell.

This invention provides a purified acylcoenzyme A: cholesterol acyltransferase related gene product II (ARGP 2). In an embodiment of the purified polypeptide, the polypeptide has the amino acid sequence set forth in FIG. 2.

This invention provides an oligonucleotide of at least 15 nucleotides capable of specifically hybridizing with a unique sequence of nucleotides present within a nucleic acid which encodes an acylcoenzyme A: cholesterol acyltransferase related gene product II (ARGP 2) diacylglycerol acyltransferase. In an embodiment of the oligonucleotide the nucleic acid which encodes an acylcoenzyme A: cholesterol acyltransferase related gene product II (ARGP 2) has the nucleic acid sequence set forth in FIG. 2. In further embodiments of the oligonucleotide the the nucleic acid may be DNA or RNA.

This invention provides a nucleic acid having a sequence complementary to the sequence of the isolated nucleic acid which encodes an acylcoenzyme A: cholesterol acyltransferase related gene product II (ARGP2 or ACAT 2).

This invention provides a transgenic, nonhuman mammal comprising the isolated nucleic acid which encodes an acylcoenzyme A: cholesterol acyltransferase related gene product II (ARGP2 or ACAT 2).

This invention provides an antibody directed to an epitope of a purified acylcoenzyme A: cholesterol acyltransferase related gene product II (ARGP 2). This invention provides an antibody capable of specifically binding to a purified acylcoenzyme A: cholesterol acyltransferase related gene product II (ARGP 2). In an embodiment of the above-identified antibodies the acylcoenzyme A: cholesterol acyltransferase related gene product II (ARGP 2) is a human acylcoenzyme A: cholesterol acyltransferase related gene product II (ARGP 2). In further embodiments the antibody is a polyclonal antibody or a monoclonal antibody.

This invention provides a pharmaceutical composition comprising an amount of any of the above-described oligonucleotides of at least 15 nucleotides capable of specifically hybridizing with a unique sequence of nucleotides present within a nucleic acid which encodes an acylcoenzyme A: cholesterol acyltransferase related gene product II (ARGP 2) diacylglycerol acyltransferase, effective to prevent overexpression of a human acylcoenzyme A: cholesterol acyltransferase related gene product II (ARGP 2) and a pharmaceutically acceptable carrier capable of passing through a cell membrane. Accordingly, the above-described pharmaceutical compositions may be used to treat hypertriglyceridemia, hyperlipidemia, heart disease and obesity.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

METHODS AND MATERIALS

General. Molecular biology techniques were performed by conventional protocols and DNA modifying reagents were purchased from Life Technologies, Inc. New England Biolabs or Promega as indicated. The PrimeIt random priming probe synthesis kit was obtained from Stratagene. The DIG Genius probe synthesis kit and CSPD were supplied by Boerhinger Mannheim. Radioactive reagents ([$^{14}$C] oleoyl-CoA, [$^{32}$P] dCTP) were purchased from Life Science Products, Inc. NEN. Ethidium bromide-stained agarose gels were visualized by the Kodak Digital Science 1D system. Automated DNA sequencing was performed at the Columbia University Cancer Center sequencing facility, and oligonucleotides were synthesized by Genset. DNA and amino acid sequence analysis and comparisons were performed using DNAStrider , PILEUP and GAP programs (GCG Inc. (21)), Prosite (22), and Identify (Ref. 23 website http://dna.stanford.edu/identify/). Yeast media components were prepared as described Screening the dbEST. A 30 amino acid ACAT concensus peptide sequence (FAEMLRFGDRMFYKDWWNSTSYSNYYRTWN) (SEQ ID NO:17) was used as the query in a tblastn (which compares a protein sequence against a nucleotide sequence data base translated in all reading frames (24, 25)) search of the data base of expressed sequence tags at NCBLI (dbEST). Three clones, H24971, R07932 and R99213, derived from a common gene (named ACAT Related Gene Product 1, ARGP1), were identified ($p<10^{-4}$). The entire human ACAT1 protein was then used in an identical search. In addition to clones of ACAT1 and ARGP1, two entries, R10272 and W76421, with significant similarity were identified ($p<10^{-5}$). They were derived from a gene we named ARGP2. Rescreening the dbEST with these clones identified two more ARGP2 entries. *Escherichia coli* clones with the largest inserts corresponding to these sequences were obtained from the I.M.A.G.E. consortium and resequenced with T3, T7, or gene specific primers.

5' Rapid Amplification of Cdna Ends (Race) of ARGP1. Oligo dT primed, double stranded cDNA was reverse transcribed from human, ileal, poly A$^+$ mRNA, kindly provided by Dr. Paul Dawson, and ligated to adapters using a commercially available kit (Clontech, Palo Alto, Calif.). Touchdown PCR (26) was performed for 35 cycles with a forward primer complementary to the adapter (AP1, 5' CCATCCTAATACGACTCACTATAGGGC) (SEQ ID NO:18) and a reverse primer (End4A, 5' CCACCTGGAGCTGGGTGAAGAAC) (SEQ ID NO:19) complementary to the ARGP1 dbEST clone Z43867. The PCR mixture included 200 nM of each oligo, 200 AM dNTPs, 1.75 mM MgCl$_2$, 2.5 units Taq, and the cDNA diluted 1:500. The 700-bp reaction product was gel isolated, ligated into YEp352 with a T overhang generated by Taq polymerase, and sequenced.

5' Race of ARGP2. A human, fetal, (20 weeks post conception) liver/spleen, oligo(dT)-primed, cDNA library in the vector PT7T3D was kindly provided by Dr. Bento Scares. PCR was performed with the cDNA, a forward primer (M13 reverse, 5' TGAGCGGATAACAATTTCACACAGG) (SEQ ID NO:20) complementary to the vector and a reverse primer (203, 5' CCCCATGCTGAGGTCTGTGATCAG) (SEQ ID NO:21), complementary to the ARGP2 dbEST clone R10272, using the above conditions. The 800 bp reaction product was gel isolated, ligated into pBS:SK (Stratagene) with a T overhang generated by Taq polymerase, and sequenced.

Hybridization Screening of a HepG2 cDNA Library. A yeast expression library of HepG2 cDNA (size selected for inserts greater than 2.0 kb in pAB23BXN, commercially available from Austral Biologicals, San Ramon, Calif.), was propagated in the *E. coli* strain MC1061 and plated onto 135- mm LB+ampicillin (50 μg/ml) plates at an approximate density of 5000 colonies per plate. Membrane (Hybond-N, Amersham) replicas of the plates were probed by hybridization with a DIG-labeled probe specific for ARGP1 (synthesized using a 420-bp NotI, PstI digestion product of the 5' RACE product) or ARGP2 (synthesized using the 5' RACE product) in 5× SSC, 0.05% SDS, 0.1% N-laurolysarcosine, 0.1 mg/ml salmon sperm DNA, and 2% (w/v) blocking reagent (Boerhinger Mannheim) at 65° C. for 14–18 hours. The membranes were washed in 0.2× SSC, 0.1% SDS at 60° C. for 80 minutes, incubated with an anti-DIG antibody (1:10,000), washed in Tris- buffered saline, incubated with the peroxidase substrate CSPD (Boerhinger Mannheim), and detected by enhanced chemi-luminescence (ECL). For ARGP1, 4 single positive clones were isolated after screening ~20,000 clones. For ARGP2, 4 single positive clones were isolated after screening ~30,000 clones. The longest clones for each were sequenced multiple times on both strands using vector and gene specific oligonucleotides.

Tissue Culture. Cultured human Caco2, HeLa, HepG2, and THP1 cell lines were donated by Dr. R. J. Deckelbaum and originally obtained from the ATCC. HepG2, HeLa, and Caco2 cells were maintained as cell monolayers in Dulbecco's modified Eagle's medium (DMEM) (Life Technologies, Inc.) +10% fetal bovine serum (FBS) (HyClone) in 5% $CO_2$. THP1 monocyte cells were maintained in suspension in RPMI (Life Technologies, Inc.) +10% fetal bovine serum (FBS) in 5% $CO_2$. Differentiation of THP1 cells was stimulated with 150 ng/ml tetramyristate phorbol ester (TPA) and 140 $\mu$M b-mercaptoethanol. Whole cell RNA was isolated from confluent monolayer cultures or pelleted THP1 cells using TRIzol (Life Technologies, Inc.) extraction. The Caco2 cells had been confluent for approximately 21 days.

Human Adult and Fetal Multi-tissue Northern Blot Analysis. Commercially obtained multi-tissue northern blot (Clontech) contained 2 $\mu$g of poly (A)$^+$ RNA from human adult or fetal (18–24 weeks postconception) tissues originally resolved on a 1.2% agarose, formaldehyde gel. The adult tissue membrane was hybridized with a random-hexamer primed, [$^{32}$P]-dCTP-labeled probe, generated using the insert of the ARGP1 dbEST clone R99213, in ExpressHyb buffer (Clontech) for 1 hour at 68° C. The membrane was washed in 0.1x SSC, 0.5% SDS at 50° C. After stripping the membrane was probed with ARGP2 (dbEST clone 10272 insert and the ARGP2 5' RACE product) using the conditions above. The fetal tissue Northern blot was hybridized with the same ARGP2 probe.

Reverse Transcription PCR. Human cDNA obtained as part of a Quick Screen cDNA Panel of Human tissues (Clontech) or reverse transcribed (Life Technologies, Inc. kit) from human ileal poly(A)$^+$ mRNA was used as the template in a PCR reaction with primers specific for ARGP1 (106, GGCATCCTGAACTGGTGTGTGGTG (SEQ ID NO:22); 110, AGCTGGCATCAGACTGTGTCTGG) (SEQ ID NO:23), ARGP2 (202, GAGTTCCCCCACATTCAT-CAAATCC (SEQ ID NO:24) ; 206, CATGCTGCTGCTCATCTTCTTTGCA) (SEQ ID NO:25) or β-actin (Act1, GAGCTGCCTGACGGCCAGGTC (SEQ ID NO:26); Act2, CACATCTGCTGGAAGGTGGACAG) (SEQ ID NO:27). The PCR mixture included 1.5 mM $MgCl_2$, 200 $\mu$M dNTPs, 400 nM of each primer, and 2 units of Taq (Life Technologies, Inc.). Following 35 cycles (94° C., 45 seconds; 60° C., 45 seconds; 72° C., 2 minutes), the products were resolved on a 1% agarose, 0.5 $\mu$g/ml ethidium bromide gel. For RNA prepared from human cultured cells, first strand cDNA synthesis was performed, with and without reverse transcriptase (SuperscriptII, Gibco) using 4 mg of whole cell RNA. A fraction of each reaction (10%) was the template in a PCR reaction (30 cycles of 94° C., 30 seconds; 68° C., 2 minutes) with primers specific for ARGP1 (103, GCTTCATGGAGTTCTGGATGGTGG (SEQ ID NO:28); 106, GGCATCCTGAACTGGTGTGTGGTG) (SEQ ID NO:29), ARGP2 (201, GACACCTCGATCTTG-GTCCTGCC (SEQ ID NO:30); 202) or human ACAT1 (ACATa, CGGAATATCAAACAGGAGCCCTTC (SEQ ID NO:31); ACATb, cATTCCAAAGAACATGAAGATGCACG) (SEQ ID NO:32).

In Vitro Assay of ACAT Activity in Yeast Microsomes. The cDNA inserts of the longest ARGP1 and ARGP2 HepG2 library clones were removed by NotI, EcoRI digestion and ligated into the yeast expression vector pRS426GP which utilizes the galactose inducible GAL1/GAL10 promoter. A cDNA corresponding to the coding region of human ACAT1 flanked by 5 bp of 5' untranslated region and 1 bp of 3' untranslated region, in pRS426GP was described previously (27). Yeast strain, SCY059 (MATα, ade2-1, can1-1, trp1-1, ura3-1, his3-11, 15, leu2-3, 112, metl4Δ14HpaI-SalI, are1ΔNA::HIS3, are2Δ::LEU2 ) with deletions in ARE1 and ARE2, the yeast homologs of human ACAT1 (4), was transformed with the above constructs or pRS426GP using lithium acetate and nucleic acid prototrophy selection (28). Expression of the constructs was verified by RT-PCR analysis of RNA isolated from the transformed cells. Culturing of the transformed yeast, induction of expression, microsome isolation, and sterol esterification assays were as described previously (previously). In those experiments involving diethylpyrocarbonate (DEPC) to modify histidine residues, a preincubation with 100 $\mu$M DEPC was performed as described (2).

RESULTS

Isolation of full length cDNA clones for two ACAT related human genes. A comparison of the human ACAT1 protein and the two yeast ACAT orthologs (Are1, Are2) identified a highly conserved (70% identical) region of 30 amino acids (ACAT1 amino acids 391–420) near the carboxyl terminus. This peptide was used to screen the data base of expressed sequence tags (dbEST). The search identified several human cDNAs, the longest being 890 bp (GenBank accession # H45923), derived from a common gene we call the ACAT Related Gene Product 1 (ARGP1). To date, 26 clones for human ARGP1 are present in the dbEST from fetal liver/spleen, infant brain, breast, cerebellum, hippocampus, kidney, placenta, testis, ovary tumor, colon tumor, and lung tumor libraries, suggesting ubiquitous and abundant expression. In addition, ARGP1 is also represented as several murine entries (e.g. GenBank accession # C75990). The dbEST was then searched using the entire ACAT1 protein sequence. Four human cDNAs, distinct from ARGP1 cDNA clones, were identified in fetal liver/spleen and fetal heart libraries and are derived from a common gene we call ARGP2. The longest entry was 600 bp (GenBank accession # R10272). To date these are the only dbEST entries for human ARGP2, although several murine entries have been identified (e.g. GenBank accession # AA410072).

Northern blot analysis of human tissues (FIGS. 3 and 4) showed that the initial dbEST clones for ARGP1 and ARGP2 were truncated, relative to the observed transcripts, by approximately 1000 and 1400 bp, respectively. To isolate full-length cDNA clones, 5' RACE was performed using cDNA synthesized from human liver (ARGP1) or ileal (ARGP2) mRNA but yielded only 600 nucleotides of novel sequence for each. The respective 5' RACE products were then used as probes to screen a size selected (>2.0 kb), HepG2 cDNA library by hybridization. The longest ARGP1 clone contained 1976 nucleotides and a 130 base poly(A)$^+$ tract which agreed with the length of the minimal ARGP1 transcript detected by Northern blot (FIG. 3). HepG2 cells express only the 2.0 kb ARGP1 transcript (Seo et al., manuscript in preparation). A similar approach identified ARGP2 clones, the longest of which contained 2040 bp of sequence with a 50 base-poly(A)$^+$ tract in accordance with the observed length of the ARGP2 transcript (FIG. 4).

ARGP1 predicted peptide The longest open reading frame (ORF) of ARGP1, flanked by a 244 nucleotide 5'-untranslated region (UTR) and a 265 nucleotide 3'-untranslated region (UTR), encodes a 488-amino acid protein (FIG. 1) with a calculated molecular mass of 55,216 daltons. The predicted initiator methionine lies within a consensus for initiation of translation (29) and downstream of an in-frame termination codon. Comparison to ACAT1 revealed 22% amino acid sequence identity (29% similarity) over the entire molecule. The conservation of these molecules is greatest towards the COOH-terminus, such that ACAT1 and ARGP1 are 28% identical over the last 250 residues. This pattern of sequence similarity is strikingly similar to that observed from comparison of ACAT1 with the yeast Are1 and Are2 proteins. ARGP1 is predicted to be a membrane bound protein with nine putative transmembrane domains and one N- linked glycosylation site. Uniquely, ARGP1 contains a diacylglycerol (DAG)/phorbol ester binding signature sequence (H . . . [FWY]. . . [KR] F . . . P) at amino acids 382–392 which was originally identified by comparison of protein kinase C isoforms and DAG kinases (FIG. 7) (36,37). This motif is also conserved in the murine homolog of ARGP1 residing at the dbEST (GenBank accession # AA764382).

ARGP2 predicted peptide The longest ARGP2 open reading frame (ORF), flanked by a 51 nucleotide 5'-UTR and a 420 nucleotide 3'- UTR, predicts a 522 amino acid protein with a calculated molecular mass of 59,942 daltons (FIG. 2). The predicted initiator methionine lies within a consensus for initiation of translation (29). Over the entire molecule, the predicted protein is 47% identical (54% similar) to human ACAT1. This conservation is even more pronounced at the COOH-terminal end of the molecules, raising to 63% identity over the last 250 residues. ARGP2 is predicted to be a membrane bound protein with seven putative transmembrane domains and two N-linked glycosylation sites. ARGP2 is similar to ACAT1 in that it contains a leucine zipper (338–359) which may mediate multimerization or interaction with other proteins. ARGP2 does not possess a predicted diacylglycerol/phorbol ester binding site. A sequenced tag entry (#WI-11660) for ARGP2 localizes to human chromosome 12, further distinguishing it from ACAT1, which is located on chromosome 1.

ARGP1 and ARGP2 expression in human tissues and tissue culture cell lines. Expression of a second ACAT would be expected in tissues (e.g. liver and intestine) which exhibit normal ACAT activity in the induced mutant ACAT1(acact⁻) mice (10). Expression of ARGP1 and ARGP2 was thus examined by Northern blot of human RNA (FIGS. 3 and 4). Hybridization of an ARGP1 cDNA probe to a panel of adult tissue mRNAs detected a transcript in all tissues examined (FIG. 3). However, ARGP1 expression levels varied qualitatively among tissues with moderate expression in thyroid, stomach, heart, skeletal muscle, and liver and high expression in adrenal cortex, adrenal medulla, testes, and small intestine. The presence of a 2.0-kb transcript was invariable among the tissues while a 2.4-kb transcript was observed in about half the tissues, most notably the tissues with high expression. The origin of these two transcripts has not been identified, however their heterogeneity is unlikely to lie at the 3' end of the message since all dbESTentries for ARGP1 cDNAs terminate at a similar position. Hybridization of the same membrane, under identical conditions, with an ARGP2 cDNA probe failed to detect a transcript in any tissue (data not shown) . Since the four ARGP2 dbEST clones were in human fetal libraries, ARGP2 expression was examined in human fetal tissues by Northern blot (FIG. 4). A 2.2 kb transcript was detected in fetal liver but not in fetal brain, lung, or kidney.

Figure 5:
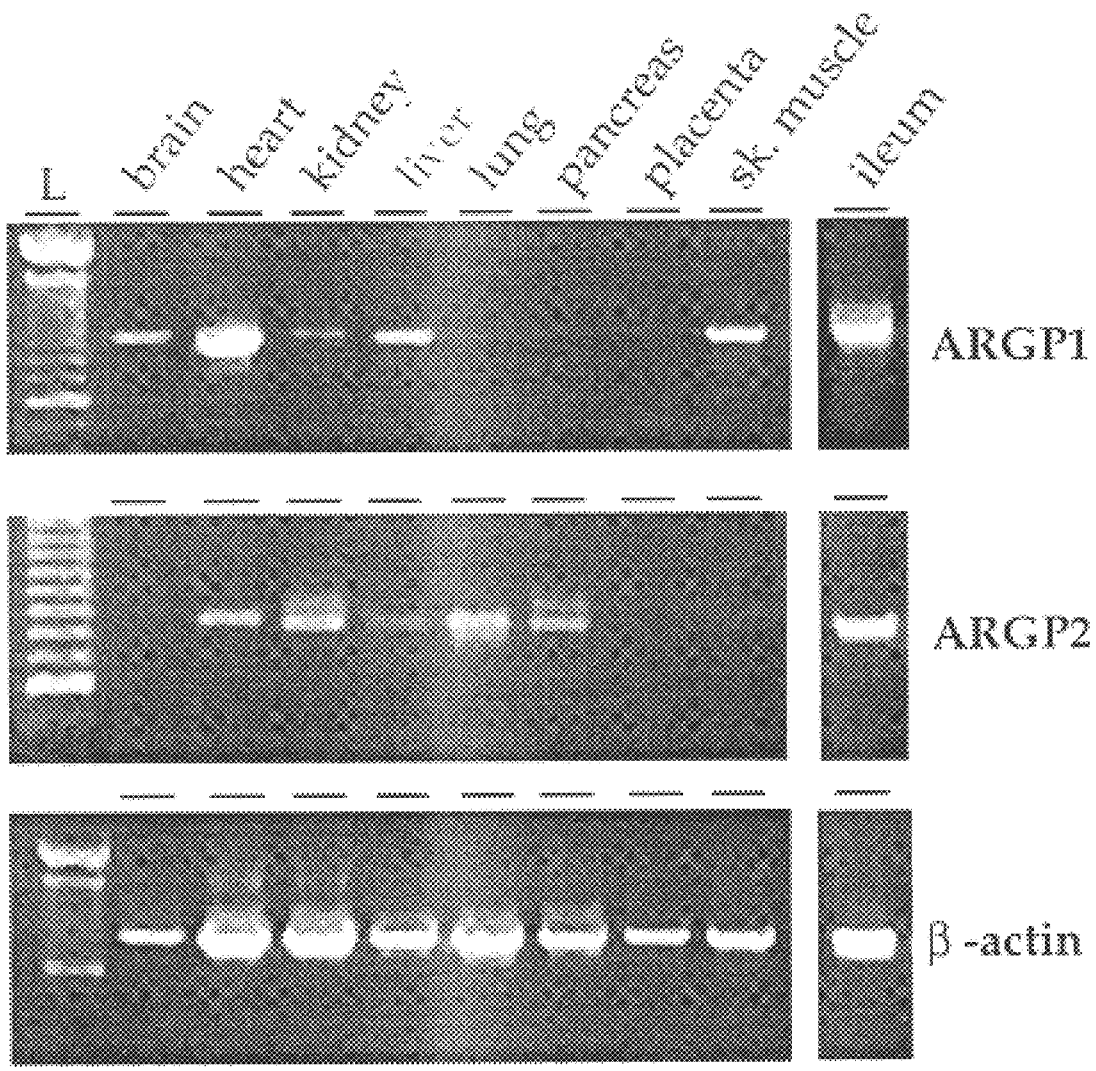
FIG. 5. Analysis of ARGP1 and ARGP2 expression in adult human tissues using RT-PCR. PCR was performed as described using a Quick Screen Human cDNA Panel (Clontech), or cDNA reverse transcribed from human ileal poly(A)$^+$ mRNA, and primers specific for ARGP1, ARGP2 or β-actin in a standard PCR cocktail. The PCR products, predicted to be 921 bp (ARGP1), 844 bp (ARGP2), or 835 bp (β-actin), were resolved on ethidium bromide stained, agarose gels with a 100 bp DNA ladder (Life Technologies, Inc.).

To further examine the expression of ACAT2 in adults, a reverse transcription - polymerase chain reaction (RT-PCR) was performed using cDNA generated from a variety of tissues (FIG. 5). As shown, ARGP2 is expressed in human adult heart, kidney, liver, lung, pancreas, and ileum. The identity of the PCR product was verified by Southern blotting and hybridization with an ARGP2- specific cDNA probe (data not shown). An RT-PCR analysis of ARGP1 on these same samples gave a similar pattern of expression to that determined by the Northern blot in FIG. 3.

Figure 6:
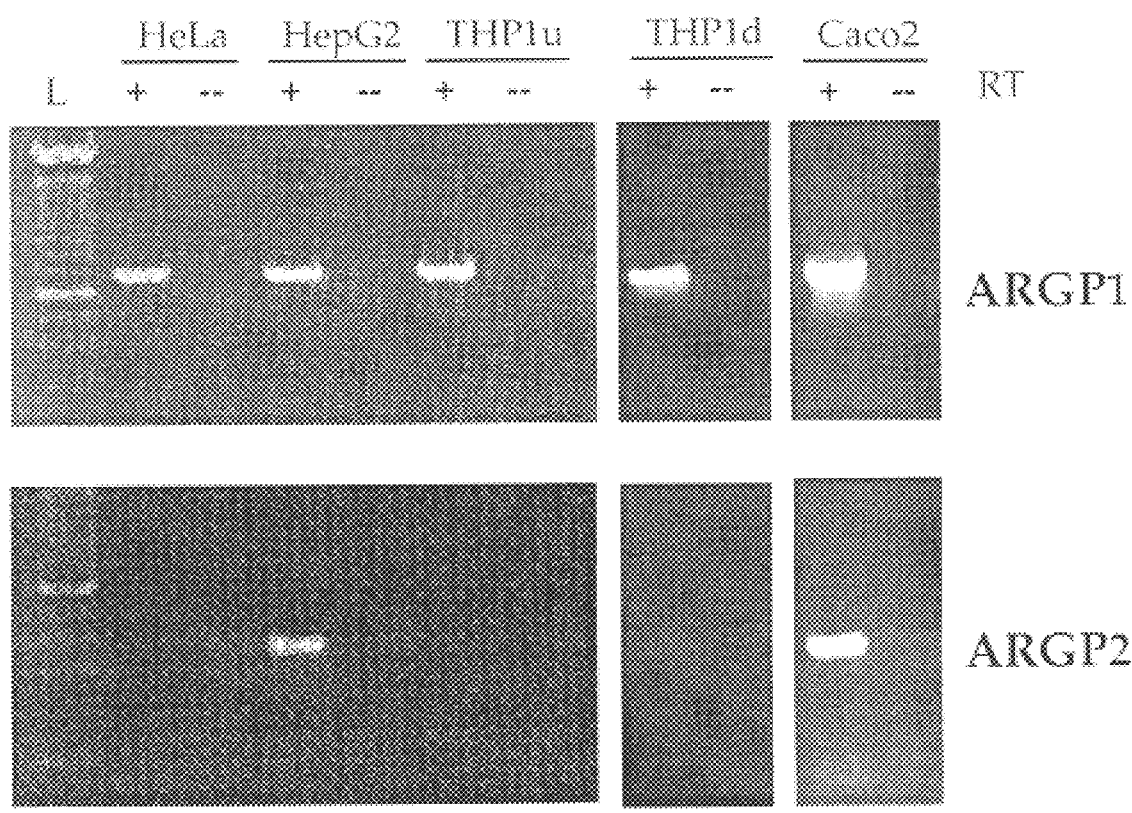
FIG. 6. Analysis of ARGP1 and ARGP2 expression in tissue culture cells using RT-PCR. Monolayer cultures of HeLa, HepG2, undifferentiated THP1 and Caco2 tissue culture cells were grown as described under "experimental details". THP1 cells were differentiated into macrophages by the addition of phorbol ester. Total cellular RNA was isolated from the cells and reverse transcribed using oligo (dT) priming in parallel with reactions which lacked reverse transcriptase (RT) enzyme. Oligonucleotide pairs complementary to ARGP1 or ARGP2 were included in a PCR using the conditions described in FIG. 5. The PCR products, predicted to be 667 bp (ARGP1) and 352 bp (ARGP2), were resolved on an ethidium bromide stained, agarose gel alongside a 100 bp DNA ladder (Life Technologies, Inc.).

ARGP1 and ARGP2 expression in human tissue culture cell lines was also examined by RT-PCR (FIG. 6). ARGP1 was expressed in cell culture models for human endothelial (HeLa), hepatocyte (HepG2), monocyte (undifferentiated THP1), macrophage (differentiated THP1) and intestinal epithelial (Caco2) cells. Expression of ARGP2 was limited to HepG2 and Caco2 cells. This reinforces the concept that ARGP1 is widely expressed while the expression of ARGP2 is more restricted. ACAT1 was expressed in all of these cell lines confirming previous observations (7, 31) (data not shown).

Assay of ACAT activity in ACAT negative yeast transformed with ARGP1 and ARGP2. The ability of ARGP1 and ARGP2 to esterify sterols was assayed in a sterol esterification deficient yeast strain (SCY059) in which the endogenous ARE genes were deleted . Microsomes from these yeast, transformed with an expression vector harboring no insert or cDNA inserts for ARGP1, ARGP2, or human ACAT1 were assayed in vitro for the incorporation of $[^{14}C]$-oleate into sterol ester. Since we previously demonstrated that cholesterol is the preferred substrate for mammalian ACAT enzymes (27, 32), assays were performed with exogenous cholesterol supplied in Triton WR-1339. As shown in Table 1, ARGP2 forms cholesterol ester at a rate of 49 pmol/minute/µg microsomal protein. This is 24-fold over background and about 15% of the activity detected in microsomes from ACAT1 transformants. We therefore renamed ARGP2 as ACAT2. ARGP1 did not display significant ACAT activity. None of the enzymes showed the ability to use ergosterol, the major sterol in yeast microsomes, as a substrate (data not shown) While the ACAT1 and ACAT2 mediated activities were equally sensitive (75% inhibition) to the ACAT inhibitor Dup128 (0.5 µM; not shown), they showed significantly different sensitivity to the histidine / tyrosine modifying agent diethylpyrocarbonate (DEPC, Table 1). This reagent was previously demonstrated to distinguish liver and adrenal ACAT activities, the latter being significantly more sensitive. Since adrenal ACAT would primarily represent ACAT1, our data are consistent with ACAT2 representing the DEPC resistant isoform identified by Kinnunen et al

TABLE 1

| cDNA Expressed | In VitroMicrosomal ACAT activity[a] | Active site Modification[b] | | |
|---|---|---|---|---|
| | | Minus DEPC | Plus DEPC (100 µm) | Degree of Inhibition |
| (no insert) | 2 +/− 2 | — | — | — |
| ACAT1 | 340 +/− 76 | 340 +/− 16 | 69 +/− 4 | 80% |
| ARGP1 | 4 +/− 3 | — | — | — |
| ACAT2 | 49 +/− 15 | 45 +/− 5 | 30 +/− 1 | 33% |

[a]Representative of Three Different Experiments On Different Preparations.
[b]Representative experiment performed in triplicate

DISCUSSION

We have isolated two independent human cDNAs, ARGP1 and ACAT2, which encode proteins with significant sequence similarities to human ACAT1. The level of nucleotide sequence conservation between ACAT1 and ACAT2 (55%) suggests their common evolution possibly arising from a gene duplication event, as clearly occurred in the case of the yeast ARE gene family. However, ARGP1 is more distantly related, bearing 39% and 43% nucleotide identity with ACAT1 and ACAT2, respectively, and may have evolved independently. The uniform similarity between the human genes and the two yeast ARE genes precludes any assignment of lineage across species.

The similarity among the three human ACAT-like proteins is most distinct over their COOH-terminal regions just as is the case when comparing the yeast Are proteins to ACAT1. The predicted ARGP1 protein displays 28% identity with ACAT1 over this portion of the molecule and includes a FY.DWWN motif present in all cloned ACATs and shown to be important for enzymatic activity (Guo et al, in preparation, FIG. 7A) However, ARGP1 is the most divergent member of this gene family. For example, a HSF motif (residues 268–270) is invariant in ACAT1 and yeast Are enzymes and was critical to ACAT1 activity in CHO cells. Replacement of Ser by Leu produced an inactive and unstable molecule (33). This motif is not conserved in ARGP1, although several serines are present in the region (e.g. $Ser_{227}$, FIG. 7B). ARGP1 is also unique in its predicted possession of a diacylglycerol / phorbol ester binding site (FIG. 7A), leading us to speculate that this enzyme might esterify diacylglycerol to produce triglyceride. Sequence similarity between diacylyglycerol acyltransferase (DGAT) and ACAT enzymes might be expected since both have a common substrate, acylCoA, but differ in the alcohol (cholesterol or diacylglycerol) used as a second substrate. Of the two new gene products described here, ACAT2 displays significantly greater sequence similarity to ACAT1, with an overall identity of 47% and 63% invariance over the COOH-terminal half of the molecules. The FY.DWWN motif common to this family of proteins is maintained in ACAT2 to the extent that the flanking residues render the tyrosine a candidate for phosphorylation as observed in ACAT1 and in yeast (FIG. 7A). Tyrosine phosphorylation may be a regulator of ACAT activity, although serine and threonine phosphorylation is unlikely to be involved . The HSF motif found in ACAT1, Are1 and Are2 is conservatively replaced in ACAT2 by YSF (residues 244–246; FIG. 7B). Interestingly, histidine modifying agents selectively inactivate adrenal microsomal ACAT activity but display a significantly higher $K_i$ (1500 µM vs. 250 µM) against liver microsomes It is intriguing to speculate that sequence variation in the (H/Y) SF motif may explain this observation. In accordance with this, we showed that ACAT1 was significantly more sensitive to DEPC than ACAT2. In common with ACAT1, Are1 and Are2, the ARGP2 sequence predicts a leucine heptad motif which may play a role in multipeptide complex formation. Radiation inactivation studies in rat liver microsomes have shown that the ACAT enzymatic complex is about 200 kDa (36, 37), much larger than the predicted monomer for ACAT 1 (65 kDa) or ACAT2 (60 kDa). There is also evidence that ACAT1 interacts with itself in a yeast two hybrid system and ACAT2 may be similar in this regard. ARGP1 and ACAT2 are also similar to ACAT1 in terms of hydrophobicity. While previous studies suggested that ACAT1 contains two transmembrane domains (6), the PredictProtein algorithm (39) indicates eight such domains in ACAT1, similar to the number predicted for ARGP1 (nine) and ARGP2 (seven). Membrane spanning domains are expected characteristics of ACAT and diacylglycerol (DGAT) enzymes since both activities are associated with microsomal membranes (40–42).

In addition to sequence similarity with ACAT1, we expect alternate ACAT enzymes to be expressed in the tissues which retain ACAT activity in the induced mutant ACAT1 mouse, namely the liver and intestine. ARGP1 met this criteria, however, it is also highly expressed in human adult adrenal cortex which was depleted of cholesterol esters in the induced mutant mouse. Monocytes from acact⁻ mice were also devoid of cholesterol ester and yet ARGP1 mRNA was detected in the human THP1 monocyte cell line. This evidence is contrary to ARGP1 being an ACAT, barring species-specific differences in expression. By the sensitive technique of RT-PCR, ACAT2 expression was observed in human adult liver and intestine and in cell culture models of the hepatocyte and intestinal enterocyte but was undetectable in THP1 monocytes and macrophages. This profile of expression is consistent with a role for ACAT2 in the livers and intestine of mammals, particularly ACAT1 knockout mice.

In confirmation of ACAT2 being a candidate for a second ACAT, heterologous expression of ACAT2 in an ACAT-negative yeast strain conferred significant microsomal cholesterol esterification with oleoyl-CoA at a level comparable to the 20–50 pmol /minute/mg protein observed in human liver microsomes supplied with exogenous cholesterol (42). The ACAT2 mediated esterification activity was significantly (85%) less than that mediated by ACAT1 in yeast. This may be due to differences in protein expression, (although both mRNAs were produced at high levels as detected by RT-PCR, data not shown), protein stability, or a genuine difference between the two enzymes.

Liver ACAT, predicted to comprise both ACAT1 and ACAT2, utilizes a limited range of sterol substrates but a wide variety (16:0, 18:0, 18:1, 18:2, and 20:4) of fatty acyl-CoAs . Determining substrate-specific differences between ACAT1 and ACAT2 may thus explain their redundancy. The redundancy may also be related to substrate affinity such as seen between the hexokinase types I–III and hexokinase type IV (glucokinase) (45). In such a scenario, one ACAT would have a lower affinity for cholesterol and only catalyze esterification at high cholesterol concentrations.

In addition to potential differences in activity, the two enzymes may have different physiological roles. For storage, cholesterol esters concentrate as cytoplasmic neutral lipid droplets, whereas for lipoprotein synthesis, cholesterol esters are incorporated into lipoprotein particles in the endoplasmic reticulum (ER) lumen. Redundant ACAT enzymes might allow one to be specific for cytoplasmic release of the cholesterol ester product and another to mediate endoplasmic reticulum (ER) lumenal release. Since lipoprotein synthesis occurs primarily in the liver and intestine, we speculate that ACAT2 may release cholesterol ester into the ER lumen, leaving ACAT1 to esterify and store sterols in the cytoplasm. The large amount of cholesterol ester, likely as cytoplasmic droplets, in the livers of high fat, high cholesterol fed acact-mice, is contrary to this hypothesis. Alternatively, ACAT2's role may be important in the fetus since it was easily detected by northern blot in human fetal liver.

The abundance of ARGP1 entries in the dbEST from a wide variety of cDNA libraries is reflective of the ubiquitous nature of ARGP1 expression in human adult tissues and tissue culture cell lines. This suggests that ARGP1 serves a function important to many cell types.

Expression of two independent clones of ARGP1 under the regulation of two yeast promoters,GAL1/10 and GAPDH (not shown), failed to detectably esterify cholesterol or ergosterol. ARGP1 specific mRNA was identified by RT-PCR in each case. We take this as further evidence that unlike ACAT1 and ACAT2, ARGP1 is not involved in cholesterol esterification, at least when expressed in yeast. Based on the conservation of amino acids in ARGP1 that are important for ACAT1 to be active, ARGP1 likely catalyzes a reaction similar to ACAT. Other esterification reactions which use fatty-acyl CoAs as substrates include retinol esterification, methyl ester formation, triterpene esterification, monoacylglycerol transferase, and diacylglycerol transferase. In the latter case our observations of a diacylglycerol binding site in ARGP1 biases us to the possibility of ARGP1 being diacylglycerol acyltransferase (DGAT), which to date has not been isolated at the molecular level. We are presently investigating whether ARGP1 can mediate these reactions.

REFERENCES

1. Maduskie, T., Billheimer, J., Germain, S., Gillies, P., Higley, C. Johnson, A., Pennev, P., Shimshick, E., and Wexler, R. (1995) *J. Med. Chem* 38, 1067–1083
2. Kinnune, P. M., DeMichele, A., and Lange, L. G. (1988) *Biochemistry* 27, 7344–7350.
3. Sturley, S. L. (1997) *Curr. Opin. Lipidol.* 8, 167–173.
4. Yang, H., Bard, M., Bruner, D. A., Gleeson, A., Deckelbaum, R. J., Aljinovic, G., Pohl, T., Rothstein, R., and Sturley, S. L. (1996) *Science* 272, 1353–1356.
5. Yu, C., Kennedy, N. J., Chang, C. C. Y., and Rothblatt, J. A. (1996) *J. Biol. Chem.* 271, 24157–24163.
6. Chang, C. C .Y., Huh, H. Y. Cadigan, K. M. and Chang, T. Y. (1993) *J. Biol. Chem.* 268, 20747–20755.
7. Uelman, P. J., Oka, K., Sullivan, M., Chang, C. C. Y., Chang, T. Y., and Chan, L. (1995) *J. Biol. Chem.* 270, 26192–26201.
8. Chang, C. C., Chen, J., Thomas, M. A., Cheng, D., Del Priore, V. A., Newton, R. S., Pape, M. E., and Chang, T. Y. (1995) *J. Biol. Chem.* 270, 29532–29540. 9. Tabas, I., Zha, X., Maxfield, F., Chang, T.- Y., Beatini, N., Farsee, R. V., and Meiner, V. (1996) *Circulation*, 94, I-35.
10. Meiner, V. M., Cases, S., Myers, H. Sande, E. R., Bellosta, S., Schambelan, M., Pitas, R. E., Mcguire, J., Herz, J., and Farses, R. V. (1996) *Proc. Natl. Acad. Sci USA* 93, 14041–14046.
11. Warner, G. J., Stoudt, G., Bamberger, M., Johnston, W. J., and Rothblatt, G. H. (1995) *J. Biol. Chem.* 270, 5772–5778.
12. Carr, T. P., Parks, J. S, and Rudel, L. L. (1992) *Arterioscler Thromb.* 12, 1275–1283.
13. Huff, M. W., Telford, D. E., Barrett, P. H. R., Billheimer, J. T., and Gillies, P. J., (1994) *Arterioscler. Thomb.* 14, 1498–1508.
14. Carr, T. P., Hamilton, R. L. J., and Rudel, L. L. (1995) *J. Lipid Res.* 36, 25–36
15. Field, F. J., Kam, M. T., and Mathur, S. N. (1990) *Gasterenterolocy* 99, 539–551.
16. Veldhuis, J. D., Strauss, J. F. d., Silavin, S. L. and Kolp, L. A. (1985) *Endocrinology* 116, 25–30.
17. Civen, M., Leeb, J., and Morin, R. J. (1982) *J. Steroid Biochem.* 16, 817–822.
18. Ausubel, F. M., Brent, R., Kingston, R. E., Moore, D. D., Seidman J. G., Smith, J. A. and Struhl, K. (1987) *Current Protocols in Molecular Biology*, 1.2 Vols, John Wiley & Sons, New York.
19. Maniatis, T. Fritsch, E. F., and Sambrook, J. (1987) Molecular Cloning Laboratory Manual. Cold Spring Harbor, Cold Spring Harbor, N.Y.
20. Marck, C. (1988) *Nucleic Acids, Res.* 16, 1829–1836.
21. Devereux, J., Haeberli, P. And Smithies, O. (1984) *Nucleic Acid Res.* 12, 387–395.
22. Bairoch, A., Bucher, P., and K. H. (1997) *Nucleic Acids Res.* 25, 217–221.
23. Nevill-Manning, C. G., Wu, T. D., and Brutlag, D. L. (1998) *Proc. Natl. Acad. Sci., USA* 95 in press.
24. Altshul, S. F., Gish, W., Miller, W., Myers, E. W., and Lipman, D. J. (1990) *J. Mol. Biol.* 218, 403–410.
25. Altshul, S. F., Madden, T. L., Schaffer, A. A., Zhang, J., Zhang, A., Miller, W. And Lipman, D. J. (1997) *Nucleic Acids. Res.* 25, 3389–3402.
26. Don, R. H., Cox, P. T. Wainwright, B. J. Baker K. And Mattick, J. S. (1991) *Nucleic Acids. Res.* 19, 4009.
27. Yang, H., Cromley, D., Wang, H., Billheimer, J. T., and Sturley, S. L. (1997) *J. Biol. Chem.* 272, 3980–3985.
28. Ito, H., Fukuda, Y., Murata, K., and Kimura, A. (1983) *J. Bacteriol* 153, 163–168.
29. Kozak, M. (1989) *J. Cell. Biol.* 108, 229–241.
30. Chang, C. C., Noll, W. W., Nutile-McMenemy, N. Lindsay, E. A., Baldini, A., Chang, W., and Chang, T. Y. (1994) *Somatic Cell Mol. Genet.* 20, 71–74.
31. Matsuda, H., Hakamata, H., Miyazaki, A., Sakai, M., Chang, C. C. Chang, T. Y. Kobori, S., Shichiri, M. And Horiuchi, S. (1996) *Biochim. Biophys. Acta* 1301, 76–84.
32. Tavani, D. M. Nes, W. R., and Billheimer, J. T. (1982) *J. Lipid Res.* 23, 774–781.
33. Cao, G., Goldstein, J. L., and Brown, M. S. (1996) *J. Biol. Chem.* 271, 14642–14648.
34. Botham, K. M. (1992) *Biochem. Soc. Trans.* 20, 454–459.
35. Corton, J. M. and Hardie, D. G. (1992) *Eur. J. Biochem.* 204, 203–208.
36. Billheimer, J. T., and Cromley, D. A. and Kempner, E. S. (1990) *J. Biol. Chem.* 265, 8632–8635.
37. Ericson, S. K., Lear, S. R., and McCreery, M. J. (1994) *J. Lipid Res.* 35, 763–769.
38. Guo, Z., Yang, H., and Sturley, S. L. (1996) *Circulation* 94, I-35.
39. Rost, B. (1996) *Methods Enzymol.* 266, 525–539.
40. Doolittle, G. M. and Chang, T. Y. (1982) *Biochemistry* 21, 674–679.
41. Goodman, D. S. Deykin, D., and Shiratori, T. (1964) *J. Biol. Chem.* 239, 1335–1344.
42. Schoonderwoerd, K., Broekhoven-Schokker, S., Huslmann, W. C., and Stam, H. (1990) *Biochem. J.* 268, 487–492.
43. Einarsson, K., Benthin, L., Ewerth, S., Hellers, G. Stahlberg, D. and Angelin, B. (1989) *J. Lipid Res.* 30, 739–746.
44. Billheimer, J. T. and Gillies, P. J. (1992) in Advances In Cholesterol Research (Esfahani, M. And Swaney, J. B., eds.) Telford Press, Philadelphia.
45. Wilson, J. E. (1995) *Rev. Physiol. Biochem. Pharmacol.* 126, 65–198

What is claimed is:

1. An isolated nucleic acid which encodes a human diacylglycerol acyltransferase (DGAT), wherein the encoded diacylglycerol acyltransferase has the same amino acid sequence as set forth in SEO ID NO:1.

2. The isolated nucleic acid of claim 1, wherein the nucleic acid is DNA or RNA.

3. The isolated nucleic acid of claim 1, wherein the nucleic acid is cDNA or genomic DNA.

4. The isolated nucleic acid of claim 1 comprising a nucleic acid sequence as set forth in SEQ ID NO: 2.

5. A vector comprising the isolated nucleic acid of claim 1.

6. The vector of claim 5 further comprising a promoter of RNA transcription operatively linked to the nucleic acid.

7. The vector of claim 6, wherein the promoter comprises a bacterial, yeast, insect or mammalian promoter.

8. The vector of claim 6, comprising a plasmid, cosmid, yeast artificial chromosome (YAC), bacteriophage or eukaryotic viral DNA.

9. A host vector system for the production of a polypeptide which comprises the vector of claim 6 in a suitable host.

10. The host vector system of claim 9, wherein the suitable host is a prokaryotic or eukaryotic cell.

11. The host vector system of claim 10, wherein the prokaryotic cell is a bacterial cell.

12. The host vector system of claim 10, wherein the eukaryotic cell is a yeast, insect, plant or mammalian cell.

13. A method for producing a polypeptide which comprises growing the host vector system of claim 9 under suitable conditions permitting production of the polypeptide and recovering the polypeptide so produced.

14. A method of obtaining a polypeptide in purified form which comprises:

(a) introducing the vector of claim 5 into a suitable host cell;

(b) culturing the resulting cell so as to produce the polypeptide;

(c) recovering the polypeptide produced in step (b); and (d) purifying the polypeptide so recovered.

* * * * *

SEQUENCE LISTING

<160> NUMBER OF SEQ ID NOS: 32

<210> SEQ ID NO 1
<211> LENGTH: 488
<212> TYPE: PRT
<213> ORGANISM: Yeast

<400> SEQUENCE: 1

```
Met Gly Asp Arg Gly Ser Ser Arg Arg Arg Thr Gly Ser Arg Pro
 1               5                  10                  15

Ser Ser His Gly Gly Gly Pro Ala Ala Glu Glu Val Arg
             20                  25              30

Asp Ala Ala Gly Pro Asp Val Gly Ala Gly Asp Ala Pro Ala
             35              40              45

Pro Ala Pro Asn Lys Asp Gly Asp Ala Gly Val Gly Ser Gly His Trp
     50              55                  60

Glu Leu Arg Cys His Arg Leu Gln Asp Ser Leu Phe Ser Ser Asp Ser
 65              70                  75                  80

Gly Phe Ser Asn Tyr Arg Gly Ile Leu Asn Trp Cys Val Val Met Leu
                 85                  90                  95

Ile Leu Ser Asn Ala Arg Leu Phe Leu Glu Asn Leu Ile Lys Tyr Gly
                100                 105                 110

Ile Leu Val Asp Pro Ile Gln Val Val Ser Leu Phe Leu Lys Asp Pro
                115                 120                 125

His Ser Trp Pro Ala Pro Cys Leu Val Ile Ala Ala Asn Val Phe Ala
        130                 135                 140

Val Ala Ala Phe Gln Val Glu Lys Arg Leu Ala Val Gly Ala Leu Thr
145                 150                 155                 160

Glu Gln Ala Gly Leu Leu Leu His Val Ala Asn Leu Ala Thr Ile Leu
                165                 170                 175

Cys Phe Pro Ala Ala Val Val Leu Leu Val Glu Ser Ile Thr Pro Val
                180                 185                 190

Gly Ser Leu Leu Ala Leu Met Ala His Thr Ile Leu Phe Leu Lys Leu
                195                 200                 205

Phe Ser Tyr Arg Asp Val Asn Ser Trp Cys Arg Arg Ala Arg Ala Lys
        210                 215                 220

Ala Ala Ser Ala Gly Lys Lys Ala Ser Ser Ala Ala Pro His Thr
225                 230                 235                 240

Val Ser Tyr Pro Asp Asn Leu Thr Tyr Arg Asp Leu Tyr Tyr Phe Leu
                245                 250                 255

Phe Ala Pro Thr Leu Cys Tyr Glu Leu Asn Phe Pro Arg Ser Pro Arg
                260                 265                 270

Ile Arg Lys Arg Phe Leu Leu Arg Arg Ile Leu Glu Met Leu Phe Phe
        275                 280                 285

Thr Gln Leu Gln Val Gly Leu Ile Gln Gln Trp Met Val Pro Thr Ile
        290                 295                 300

Gln Asn Ser Met Lys Pro Phe Lys Asp Met Asp Tyr Ser Arg Ile Ile
305                 310                 315                 320

Glu Arg Leu Leu Lys Leu Ala Val Pro Asn His Leu Ile Trp Leu Ile
                325                 330                 335

Phe Phe Tyr Trp Leu Phe His Ser Cys Leu Asn Ala Val Ala Glu Leu
                340                 345                 350

Met Gln Phe Gly Asp Arg Glu Phe Tyr Arg Asp Trp Trp Asn Ser Glu
```

```
              355                 360                 365
    Ser Val Thr Tyr Phe Trp Gln Asn Trp Asn Ile Pro Val His Lys Trp
                370                 375                 380

Cys Ile Arg His Phe Tyr Lys Pro Met Leu Arg Arg Gly Ser Ser Lys
    385                 390                 395                 400

Trp Met Ala Arg Thr Gly Val Phe Leu Ala Ser Ala Phe Phe His Glu
                    405                 410                 415

Tyr Leu Val Ser Val Pro Leu Arg Met Phe Arg Leu Trp Ala Phe Thr
                420                 425                 430

Gly Met Met Ala Gln Ile Pro Leu Ala Trp Phe Val Gly Arg Phe Phe
                    435                 440                 445

Gln Gly Asn Tyr Gly Asn Ala Ala Val Trp Leu Ser Leu Ile Ile Gly
                450                 455                 460

Gln Pro Ile Ala Val Leu Met Tyr Val His Asp Tyr Tyr Val Leu Asn
    465                 470                 475                 480

Tyr Glu Ala Pro Ala Ala Glu Ala
                    485

<210> SEQ ID NO 2
<211> LENGTH: 1976
<212> TYPE: DNA
<213> ORGANISM: Yeast

<400> SEQUENCE: 2
gaatggacga gagaggcggc cgtccattag ttagcggctc cggagcaacg cagccgttgt      60
ccttgaggcc gacgggcctg acgcgggcgg gttgaacgcg ctggtgaggc ggtcacccgg     120
gctacggcgg ccggcagggg gcagtggcgg ccgttgtcta gggcccggag gtggggccgc     180
gcgcctcggg cgctacgaac ccggcaggcc cacgcttggc tgcggccggg tgcgggctga     240
ggccatgggc gaccgcggca gctcccggcg ccggaggaca gggtcgcggc cctcgagcca     300
cggcggcggc gggcctgcgg cggcggaaga agaggtgcgg gacgccgctg cgggccccga     360
cgtgggagcc gcggggacg cgccagcccc ggcccccaac aaggacggag acgccggcgt      420
gggcagcggc cactgggagc tgaggtgcca tcgcctgcag gattctttat tcagctctga     480
cagtggcttc agcaactacc gtggcatcct gaactggtgt gtggtgatgc tgatcttgag     540
caatgcccgg ttatttctgg agaacctcat caagtatggc atcctggtgg accccatcca     600
ggtggtttct ctgttcctga aggatcccca tagctggccc gccccatgcc tggttattgc     660
ggccaatgtc tttgctgtgg ctgcattcca ggttgagaag cgcctggcgg tgggtgccct     720
gacggagcag gcgggactgc tgctgcacgt agccaacctg gccaccattc tgtgtttccc     780
agcggctgtg gtcttactgg ttgagtctat cactccagtg ggctccctgc tggcgctgat     840
ggcgcacacc atcctcttcc tcaagctctt ctcctaccgc gacgtcaact catggtgccg     900
cagggccagg gccaaggctg cctctgcagg gaagaaggcc agcagtgctg ctgccccgca     960
caccgtgagc tacccggaca atctgaccta ccgcgatctc tactacttcc tcttcgcccc    1020
caccttgtgc tacgagctca actttccccg ctctccccgc atccggaagc gctttctgct    1080
gcgacggatc cttgagatgc tgttcttcac ccagctccag gtggggctga tccagcagtg    1140
gatggtcccc accatccaga actccatgaa gcccttcaag gacatggact actcacgcat    1200
catcgagcgc ctcctgaagc tggcggtccc caatcacctc atctggctca tcttcttcta    1260
ctggctcttc cactcctgcc tgaatgccgt ggctgagctc atgcagtttg agaccggga     1320 gttctaccgg gactggtgga actccgagtc tgtcacctac ttctggcaga actggaacat    1380
```

-continued

```
cctgtgcac aagtggtgca tcagacactt ctacaagccc atgcttcgac ggggcagcag    1440
caagtggatg ccaggacag  gggtgttcct ggcctcggct ttcttccacg agtacctggt    1500
gagcgtccct ctgcgaatgt tccgcctctg ggctttcacg ggcatgatgg ctcagatccc    1560
actggcctgg ttcgtgggcc gctttttcca gggcaactat ggcaacgcag ctgtgtggct    1620
gtcgctcatc atcggacagc caatagccgt cctcatgtac gtccacgact actacgtgct    1680
caactatgag gccccagcgg cagaggcctg agctgcacct gagggcctgg cttctcactg    1740
ccacctcaaa cccgctgcca gagcccacct ctcctcctag gcctcgagtg ctggggatgg    1800
gcctggctgc acagcatcct cctctggtcc cagggaggcc tctctgccct atggggctct    1860
gtcctgcacc cctcagggat ggcgacagca ggccagacac agtctgatgc cagctgggag    1920
tcttgctgac cctgccccgg gtccgagggt gtcaataaag tgctgtccag tgggag       1976
```

<210> SEQ ID NO 3
<211> LENGTH: 522
<212> TYPE: PRT
<213> ORGANISM: Yeast

<400> SEQUENCE: 3

```
Met Glu Pro Gly Gly Ala Arg Leu Arg Leu Gln Arg Thr Glu Gly Leu
  1               5                  10                  15

Gly Gly Glu Arg Glu Arg Gln Pro Cys Gly Asp Gly Asn Thr Glu Thr
             20                  25                  30

His Arg Ala Pro Asp Leu Val Gln Trp Thr Arg His Met Glu Ala Val
         35                  40                  45

Lys Ala Gln Leu Leu Glu Gln Ala Gln Gly Gln Leu Arg Glu Leu Leu
     50                  55                  60

Asp Arg Ala Met Arg Glu Ala Ile Gln Ser Tyr Pro Ser Gln Asp Lys
 65                  70                  75                  80

Pro Leu Pro Pro Pro Pro Gly Ser Leu Ser Arg Thr Gln Glu Pro
                 85                  90                  95

Ser Leu Gly Lys Gln Lys Val Phe Ile Ile Arg Lys Ser Leu Leu Asp
            100                 105                 110

Glu Leu Met Glu Val Gln His Phe Arg Thr Ile Tyr His Met Phe Ile
        115                 120                 125

Ala Gly Leu Cys Val Phe Ile Ile Ser Thr Leu Ala Ile Asp Phe Ile
    130                 135                 140

Asp Glu Gly Arg Leu Leu Leu Glu Phe Asp Leu Leu Ile Phe Ser Phe
145                 150                 155                 160

Gly Gln Leu Pro Leu Ala Leu Val Thr Trp Val Pro Met Phe Leu Ser
                165                 170                 175

Thr Leu Leu Ala Pro Tyr Gln Ala Leu Arg Leu Trp Ala Arg Gly Thr
            180                 185                 190

Trp Thr Gln Ala Thr Gly Leu Gly Cys Ala Leu Leu Ala Ala His Ala
        195                 200                 205

Val Val Leu Cys Ala Leu Pro Val His Val Ala Val Glu His Gln Leu
    210                 215                 220

Pro Pro Ala Ser Arg Cys Val Leu Val Phe Glu Gln Val Arg Phe Leu
225                 230                 235                 240

Met Lys Ser Tyr Ser Phe Leu Arg Glu Ala Val Pro Gly Thr Leu Arg
                245                 250                 255

Ala Arg Arg Gly Glu Gly Ile Gln Ala Pro Ser Phe Ser Ser Tyr Leu
            260                 265                 270
```

-continued

```
Tyr Phe Leu Phe Cys Pro Thr Leu Ile Tyr Arg Glu Thr Tyr Pro Arg
            275                 280                 285
Thr Pro Tyr Val Arg Trp Asn Tyr Val Ala Lys Asn Phe Ala Gln Ala
    290                 295                 300
Leu Gly Cys Val Leu Tyr Ala Cys Phe Ile Leu Gly Arg Leu Cys Val
305                 310                 315                 320
Pro Val Phe Ala Asn Met Ser Arg Glu Pro Phe Ser Thr Arg Ala Leu
                325                 330                 335
Val Leu Ser Ile Leu His Ala Thr Leu Pro Gly Ile Phe Met Leu Leu
            340                 345                 350
Leu Ile Phe Phe Ala Phe Leu His Cys Trp Leu Asn Ala Phe Ala Glu
            355                 360                 365
Met Leu Arg Phe Gly Asp Arg Met Phe Tyr Arg Asp Trp Trp Asn Ser
    370                 375                 380
Thr Ser Phe Ser Asn Tyr Tyr Arg Thr Trp Asn Val Val His Asp
385                 390                 395                 400
Trp Leu Tyr Ser Tyr Val Tyr Gln Asp Gly Leu Arg Leu Leu Gly Ala
                405                 410                 415
Arg Ala Arg Gly Val Ala Met Leu Gly Val Phe Leu Val Ser Ala Val
            420                 425                 430
Ala His Glu Tyr Ile Phe Cys Phe Val Leu Gly Phe Phe Tyr Pro Val
            435                 440                 445
Met Leu Ile Leu Phe Leu Val Ile Gly Gly Met Leu Asn Phe Met Met
    450                 455                 460
His Asp Gln Arg Thr Gly Pro Ala Trp Asn Val Leu Met Trp Thr Met
465                 470                 475                 480
Leu Phe Leu Gly Gln Gly Ile Gln Val Ser Leu Tyr Cys Gln Glu Trp
                485                 490                 495
Tyr Ala Arg Arg His Cys Pro Leu Pro Gln Ala Thr Phe Trp Gly Leu
            500                 505                 510
Val Thr Pro Arg Ser Trp Ser Cys His Thr
            515                 520
```

<210> SEQ ID NO 4
<211> LENGTH: 2040
<212> TYPE: DNA
<213> ORGANISM: Yeast

<400> SEQUENCE: 4

```
agaagaggca acacgggcaa gggctgcctg ctgcccgctg gagaccgcac catggagcca      60
ggcggggccc gtctgcgtct gcagaggaca gaagggctgg gaggggagcg ggagcgccaa     120
ccctgtggag atggaaacac tgagacgcac agagccccgg acttggtaca atggacccga     180
cacatggagg ctgtgaaggc acaattgctg agcaagcgc agggacaact gagggagctg     240
ctggatcggg ccatgcggga ggctatacaa tcctacccat cacaagacaa acctctgccc     300
ccacctcccc caggttcctt gagcaggacc caggagccat ccctgggaa acagaaagtt     360
ttcatcatcc gcaagtccct gcttgatgag ctgatggagg tgcagcattt ccgcaccatc     420
taccacatgt tcatcgctgg cctgtgtgtc ttcatcatca gcaccctggc catcgacttc     480
attgatgagg gcaggctgct gctggagttt gacctactga tcttcagctt cggacagctg     540
ccattggcgc tggtgacctg ggtgcccatg tttctgtcca ccctgttggc gccgtaccag     600
gccctacggc tgtgggccag gggcacctgg acgcaggcga cgggcctggg ctgtgcgctg     660
```

-continued

```
ctagccgccc acgccgtggt gctctgcgcg ctgccggtcc acgtggccgt ggagcatcag    720
ctcccgccgg cctcccgttg tgtcctggtc ttcgagcagg ttaggttcct gatgaaaagc    780
tactccttcc tgagagaggc tgtgcctggg acccttcgtg ccagacgagg tgaggggatc    840
caggccccca gtttctccag ctacctctac ttcctcttct gcccaacact catctacagg    900
gagacttacc ctaggacgcc ctatgtcagg tggaattatg tggccaagaa ctttgcccag    960
gccctgggat gtgtgctcta tgcctgcttc atcctgggcc gcctctgtgt tcctgtcttt   1020
gccaacatga gccgagagcc cttcagcacc cgtgccctgg tgctctctat cctgcatgcc   1080
acgttgccag gcatcttcat gctgctgctc atcttctttg ccttcctcca ttgctggctc   1140
aacgcctttg ccgagatgct acgatttgga gacaggatgt tctaccggga ctggtggaac   1200
tcaacgtcct tctccaacta ctaccgcact tggaacgtgg tggtccatga ctggctgtac   1260
agctacgtgt atcaggatgg gctgcggctc cttggtgccc gggcccgagg ggtagccatg   1320
ctgggtgtgt tcctggtctc cgcagtggcc catgagtata tcttctgctt cgtcctgggg   1380
ttcttctatc ccgtcatgct gatactcttc cttgtcattg gaggaatgtt gaacttcatg   1440
atgcatgacc agcgcaccgg cccggcatgg aacgtgctga tgtggaccat gctgtttcta   1500
ggccagggaa tccaggtcag cctgtactgc caggagtggt acgcacggcg gcactgcccc   1560
ttaccccagg caactttctg ggggctggtg acacctcgat cttggtcctg ccatacctag   1620
aggtcgggac agacgacgct acctgcccag acaccaccaa gttctctgcc tgcaaaacct   1680
ggggaccagg actccctgtc tgcattcccc aaatttggct ctgagtcgag caacctgca    1740 cacaagaccc ccacccaagg aatgtgcaag gactgagatc tgcagacttg tgggtaactg   1800
atcacagacc tcagcatggg ggtgaccagg gtgactcttc aatccctatc ccatgggct    1860 gggtacagga tatcctccta ccccatgact gtcttaggga gacttggggt accttatgga   1920
tttgatgaat gtgggggaac tcagaggaac tggggccacc aaggttggaa aagggtttgg   1980
ttcttgactt tgtattcctt ccaatacagc aataaacttt gtctcccttt ttattcattc   2040
```

<210> SEQ ID NO 5
<211> LENGTH: 52
<212> TYPE: PRT
<213> ORGANISM: Yeast

<400> SEQUENCE: 5

Glu Leu Thr Arg Phe Ala Asp Arg Tyr Phe Tyr Gly Asp Trp Trp Asn
1               5                   10                  15

Cys Val Ser Phe Glu Glu Phe Ser Arg Ile Trp Asn Val Pro Val His
        20                  25                  30

Lys Phe Leu Leu Arg His Val Tyr His Ser Ser Met Gly Ala Leu His
    35                  40                  45

Leu Ser Lys Ser
    50

<210> SEQ ID NO 6
<211> LENGTH: 52
<212> TYPE: PRT
<213> ORGANISM: Yeast

<400> SEQUENCE: 6

Glu Leu Thr Arg Phe Gly Asp Arg Tyr Phe Tyr Gly Asp Trp Trp Asn
1               5                   10                  15

Cys Val Ser Trp Ala Asp Phe Ser Arg Ile Trp Asn Ile Pro Val His
        20                  25                  30

-continued

Lys Phe Leu Leu Arg His Val Tyr His Ser Ser Met Ser Phe Lys
        35                  40                  45
Leu Asn Lys Ser
    50

<210> SEQ ID NO 7
<211> LENGTH: 53
<212> TYPE: PRT
<213> ORGANISM: human

<400> SEQUENCE: 7

Glu Met Leu Arg Phe Gly Asp Arg Met Phe Tyr Lys Asp Trp Trp Asn
 1               5                  10                  15
Ser Thr Ser Tyr Ser Asn Tyr Arg Thr Trp Asn Val Val His
            20                  25                  30
Asp Trp Leu Tyr Tyr Ala Tyr Lys Asp Phe Leu Trp Phe Phe Ser
        35                  40                  45
Lys Arg Phe Lys Ser
    50

<210> SEQ ID NO 8
<211> LENGTH: 53
<212> TYPE: PRT
<213> ORGANISM: human

<400> SEQUENCE: 8

Glu Met Leu Arg Phe Gly Asp Arg Met Phe Tyr Arg Asp Trp Trp Asn
 1               5                  10                  15
Ser Thr Ser Phe Ser Asn Tyr Tyr Arg Thr Trp Asn Val Val His
            20                  25                  30
Asp Trp Leu Tyr Ser Tyr Val Tyr Gln Asp Gly Leu Arg Leu Leu Gly
        35                  40                  45
Ala Arg Ala Arg Gly
    50

<210> SEQ ID NO 9
<211> LENGTH: 51
<212> TYPE: PRT
<213> ORGANISM: human

<400> SEQUENCE: 9

Glu Leu Met Gln Phe Gly Asp Arg Glu Phe Tyr Arg Asp Trp Trp Asn
 1               5                  10                  15
Ser Glu Ser Val Thr Tyr Phe Trp Gln Asn Trp Asn Ile Pro Val His
            20                  25                  30
Lys Trp Cys Ile Arg His Phe Tyr Lys Pro Met Leu Arg Arg Gly Ser
        35                  40                  45
Ser Lys Trp
    50

<210> SEQ ID NO 10
<211> LENGTH: 33
<212> TYPE: PRT
<213> ORGANISM: consensus

<400> SEQUENCE: 10

Glu Leu Arg Phe Gly Asp Arg Phe Tyr Asp Trp Trp Asn Ser Ser Phe
 1               5                  10                  15
Arg Trp Asn Val Pro Val His Lys Trp Leu Arg His Val Tyr Leu Lys

-continued

```
                20                  25                  30
Ser

SEQ ID NO 11
<211> LENGTH: 20
<212> TYPE: PRT
<213> ORGANISM: Yeast

<400> SEQUENCE: 11

Phe Val Met Lys Ser His Ser Phe Ala Phe Tyr Asn Gly Tyr Leu Trp
 1               5                  10                  15

Asp Ile Lys Gln
            20

<210> SEQ ID NO 12
<211> LENGTH: 20
<212> TYPE: PRT
<213> ORGANISM: Yeast

<400> SEQUENCE: 12

Leu Leu Met Lys Met His Ser Phe Ala Phe Tyr Asn Gly Tyr Leu Trp
 1               5                  10                  15

Gly Ile Lys Glu
            20

<210> SEQ ID NO 13
<211> LENGTH: 20
<212> TYPE: PRT
<213> ORGANISM: human

<400> SEQUENCE: 13

Phe Val Met Lys Ala His Ser Phe Val Arg Glu Asn Val Pro Arg Val
 1               5                  10                  15

Leu Asn Ser Ala
            20

<210> SEQ ID NO 14
<211> LENGTH: 19
<212> TYPE: PRT
<213> ORGANISM: human

<400> SEQUENCE: 14

Phe Leu Met Lys Ser Tyr Ser Phe Leu Arg Glu Ala Val Pro Gly Thr
 1               5                  10                  15

Leu Arg Ala

<210> SEQ ID NO 15
<211> LENGTH: 17
<212> TYPE: PRT
<213> ORGANISM: human

<400> SEQUENCE: 15

Phe Leu Lys Leu Phe Ser Tyr Arg Asp Val Asn Ser Trp Cys Arg Arg
 1               5                  10                  15

Ala

<210> SEQ ID NO 16
<211> LENGTH: 15
<212> TYPE: PRT
<213> ORGANISM: consensus
```

```
<400> SEQUENCE: 16

Phe Leu Met Lys Ser His Ser Phe Ala Asn Leu Trp Leu Ile Ala
 1               5                  10                  15

<210> SEQ ID NO 17
<211> LENGTH: 30
<212> TYPE: PRT
<213> ORGANISM: consensus

<400> SEQUENCE: 17

Phe Ala Glu Met Leu Arg Phe Gly Asp Arg Met Phe Tyr Lys Asp Trp
 1               5                  10                  15

Trp Asn Ser Thr Ser Tyr Ser Asn Tyr Tyr Arg Thr Trp Asn
                20                  25                  30

<210> SEQ ID NO 18
<211> LENGTH: 27
<212> TYPE: DNA
<213> ORGANISM: human

<400> SEQUENCE: 18
ccatcctaat acgactcact atagggc                                27

<210> SEQ ID NO 19
<211> LENGTH: 23
<212> TYPE: DNA
<213> ORGANISM: human

<400> SEQUENCE: 19
ccacctggag ctgggtgaag aac                                    23

<210> SEQ ID NO 20
<211> LENGTH: 25
<212> TYPE: DNA
<213> ORGANISM: human

<400> SEQUENCE: 20
tgagcggata acaatttcac acagg                                  25

<210> SEQ ID NO 21
<211> LENGTH: 24
<212> TYPE: DNA
<213> ORGANISM: human

<400> SEQUENCE: 21
ccccatgctg aggtctgtga tcag                                   24

<210> SEQ ID NO 22
<211> LENGTH: 24
<212> TYPE: DNA
<213> ORGANISM: human

<400> SEQUENCE: 22
ggcatcctga actggtgtgt ggtg                                   24

<210> SEQ ID NO 23
<211> LENGTH: 23
<212> TYPE: DNA
<213> ORGANISM: human

<400> SEQUENCE: 23
agctggcatc agactgtgtc tgg                                    23
```

```
<210> SEQ ID NO 24
<211> LENGTH: 25
<212> TYPE: DNA
<213> ORGANISM: human

<400> SEQUENCE: 24
gagttccccc acattcatca aatcc                                              25

<210> SEQ ID NO 25
<211> LENGTH: 25
<212> TYPE: DNA
<213> ORGANISM: human

<400> SEQUENCE: 25
catgctgctg ctcatcttct ttgca                                              25

<210> SEQ ID NO 26
<211> LENGTH: 21
<212> TYPE: DNA
<213> ORGANISM: human

<400> SEQUENCE: 26
gagctgcctg acggccaggt c                                                  21

<210> SEQ ID NO 27
<211> LENGTH: 23
<212> TYPE: DNA
<213> ORGANISM: human

<400> SEQUENCE: 27
cacatctgct ggaaggtgga cag                                                23

<210> SEQ ID NO 28
<211> LENGTH: 24
<212> TYPE: DNA
<213> ORGANISM: human

<400> SEQUENCE: 28
gcttcatgga gttctggatg gtgg                                               24

<210> SEQ ID NO 29
<211> LENGTH: 24
<212> TYPE: DNA
<213> ORGANISM: human

<400> SEQUENCE: 29
ggcatcctga actggtgtgt ggtg                                               24

<210> SEQ ID NO 30
<211> LENGTH: 23
<212> TYPE: DNA
<213> ORGANISM: human

<400> SEQUENCE: 30
gacacctcga tcttggtcct gcc                                                23

<210> SEQ ID NO 31
<211> LENGTH: 24
<212> TYPE: DNA
<213> ORGANISM: human

<400> SEQUENCE: 31
cggaatatca aacaggagcc cttc                                               24
```

```
<210> SEQ ID NO 32
<211> LENGTH: 26
<212> TYPE: DNA
<213> ORGANISM: human

<400> SEQUENCE: 32
cattccaaag aacatgaaga tgcacg                                          26
```